US008352041B2

(12) United States Patent
Das et al.

(10) Patent No.: US 8,352,041 B2
(45) Date of Patent: Jan. 8, 2013

(54) REMOTE CONTROLS AND AMBULATORY MEDICAL SYSTEMS INCLUDING THE SAME

(75) Inventors: Stephen D. Das, Santa Clarita, CA (US); Jose P. Bernardo, Woodland Hills, CA (US); Daniel H. Villegas, Granada Hills, CA (US); Scott R. Gibson, Granada Hills, CA (US); Timothy John Payne, Santa Ana, CA (US); Scott LaVoy Conway, Yorba Linda, CA (US); Joseph Wayne Vandegriff, Lago Vista, TX (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 1308 days.

(21) Appl. No.: 11/564,219

(22) Filed: Nov. 28, 2006

(65) Prior Publication Data

US 2008/0125064 A1 May 29, 2008

Related U.S. Application Data

(60) Provisional application No. 60/867,580, filed on Nov. 28, 2006.

(51) Int. Cl.
*A61N 1/08* (2006.01)

(52) U.S. Cl. ................ 607/60; 607/30; 607/31; 607/32; 604/890.1; 604/891.1; 604/131; 604/132; 604/133; 604/134; 604/135; 604/136; 604/137; 604/138; 604/139; 604/140; 604/141; 604/142; 604/143; 604/144; 604/145; 604/146; 604/147; 604/148; 604/149; 604/150; 604/151; 604/152; 604/153; 604/154; 604/155

(58) Field of Classification Search .................. 600/424; 378/117; 604/151; 128/903; 709/203; 340/5.61–5.64, 4.3, 12.22; 341/176; 345/169; 348/734; 455/41.1, 66.1, 419–420; 707/769; 713/323; 725/38–40
See application file for complete search history.

(56) References Cited

U.S. PATENT DOCUMENTS

| | | | | |
|---|---|---|---|---|
| 3,770,925 | A * | 11/1973 | Nelson et al. | 200/296 |
| 3,822,708 | A | 7/1974 | Zilber | |
| 4,365,633 | A * | 12/1982 | Loughman et al. | 607/30 |
| 4,387,718 | A | 6/1983 | Bilitz | |
| 4,810,996 | A | 3/1989 | Glen et al. | |

(Continued)

FOREIGN PATENT DOCUMENTS

EP 1 585 080 A2 10/2005

(Continued)

OTHER PUBLICATIONS

PCT Int. Search Report and Written Opinion dated Jun. 9, 2008 for PCT App. No. PCT/US07/085659.

(Continued)

*Primary Examiner* — Carl H Layno
*Assistant Examiner* — Paula J Stice
(74) *Attorney, Agent, or Firm* — Henricks, Slavin & Holmes LLP

(57) ABSTRACT

Remote controls, including a communication device, a button or other communication device actuator and a movable structure that allows actuation of the actuator in one position and prevents actuation of the actuator in another position to prevent inadvertent signal transmission.

32 Claims, 13 Drawing Sheets

U.S. PATENT DOCUMENTS

| | | | | |
|---|---|---|---|---|
| 4,855,746 | A | 8/1989 | Stacy | |
| 5,021,616 | A | 6/1991 | Hardt | |
| 5,442,679 | A | 8/1995 | Regis et al. | |
| 5,478,211 | A | 12/1995 | Dominiak | |
| 5,620,483 | A | 4/1997 | Minogue | |
| 5,683,350 | A * | 11/1997 | Paul et al. | 600/249 |
| 5,711,302 | A | 1/1998 | Lampropoulos | |
| 5,732,135 | A | 3/1998 | Weadon et al. | |
| 5,755,737 | A * | 5/1998 | Prieve et al. | 607/4 |
| 5,800,333 | A | 9/1998 | Liprie | |
| 6,106,576 | A | 8/2000 | Fromson | |
| 6,141,574 | A | 10/2000 | Satherley | |
| 6,283,944 | B1 | 9/2001 | McMullen et al. | |
| 6,400,990 | B1 | 6/2002 | Silvian | |
| 6,427,088 | B1 | 7/2002 | Bowman et al. | |
| 6,562,001 | B2 | 5/2003 | Lebel et al. | |
| 6,669,668 | B1 * | 12/2003 | Kleeman et al. | 604/131 |
| 6,687,547 | B2 | 2/2004 | Goedeke et al. | |
| 6,768,425 | B2 | 7/2004 | Flaherty et al. | |
| 6,934,220 | B1 * | 8/2005 | Cruitt et al. | 368/10 |
| 7,060,031 | B2 | 6/2006 | Webb et al. | |
| 7,453,346 | B2 * | 11/2008 | Buccinna et al. | 340/5.72 |
| 7,604,176 | B2 * | 10/2009 | Bates et al. | 235/486 |
| 8,162,923 | B2 * | 4/2012 | Adams et al. | 604/890.1 |
| 2002/0058906 | A1 | 5/2002 | Lebel et al. | |
| 2002/0126036 | A1 | 9/2002 | Flaherty et al. | |
| 2002/0177809 | A1 * | 11/2002 | Kriesel et al. | 604/132 |
| 2003/0181852 | A1 | 9/2003 | Mann et al. | |
| 2004/0015131 | A1 * | 1/2004 | Flaherty et al. | 604/123 |
| 2004/0027296 | A1 * | 2/2004 | Gerber | 343/702 |
| 2004/0128161 | A1 | 7/2004 | Mazar et al. | |
| 2004/0183671 | A1 | 9/2004 | Long | |
| 2004/0230247 | A1 | 11/2004 | Stein | |
| 2004/0249477 | A1 | 12/2004 | Blanpain | |
| 2005/0012594 | A1 | 1/2005 | Shim | |
| 2005/0126897 | A1 * | 6/2005 | Stephens | 200/5 A |
| 2005/0215982 | A1 | 9/2005 | Malave et al. | |
| 2005/0246006 | A1 | 11/2005 | Daniels | |
| 2005/0251228 | A1 | 11/2005 | Hamel | |
| 2006/0202881 | A1 | 9/2006 | Buccinna | |
| 2006/0244627 | A1 | 11/2006 | Kagermeier et al. | |
| 2007/0034213 | A1 | 2/2007 | Poisner | |
| 2007/0054651 | A1 | 3/2007 | Farmer | |
| 2007/0060869 | A1 | 3/2007 | Tolle et al. | |
| 2007/0100302 | A1 * | 5/2007 | Dicarlo et al. | 604/288.01 |
| 2007/0255348 | A1 | 11/2007 | Holtzclaw | |
| 2008/0125065 | A1 | 5/2008 | Das | |
| 2009/0240240 | A1 * | 9/2009 | Hines et al. | 604/890.1 |

FOREIGN PATENT DOCUMENTS

| | | | |
|---|---|---|---|
| WO | WO 03/026726 | A1 | 4/2003 |
| WO | WO 2004/028596 | A1 | 4/2004 |
| WO | WO 2005/061048 | A1 | 7/2005 |

OTHER PUBLICATIONS

Office Action dated May 5, 2010 in U.S. Appl. No. 11/564,229.
Office Action dated Jul. 27, 2010 in U.S. Appl. No. 11/564,229.
Office Action dated Jan. 20, 2011 in U.S. Appl. No. 11/564,229.
Office Action dated Jun. 27, 2011 in U.S. Appl. No. 11/564,229.
Office Action dated Mar. 22, 2012 in U.S. Appl. No. 11/564,229.

* cited by examiner

REMOTE CONTROLS AND AMBULATORY MEDICAL SYSTEMS INCLUDING THE SAME

CROSS-REFERENCE TO RELATED APPLICATIONS

This application is related to commonly-owned U.S. application Ser. No. 60/867,580, filed Nov. 28, 2006 and entitled "Method, Apparatus and System for Assigning Remote Control Device to Ambulatory Medical Device."

This application is also related to commonly-owned and concurrently filed U.S. application Ser. No. 11/564,229, filed Nov. 28, 2006 and entitled "Remote Controls and Ambulatory Medical Systems Including the Same."

BACKGROUND OF THE INVENTIONS

1. Field of Inventions

The present inventions relate generally to remote controls and ambulatory medical systems including remote controls.

2. Description of the Related Art

Many medical systems include a therapeutic device and a remote control with a plurality of buttons that allows a physician, technician or patient to provide an instruction to the therapeutic device by way of a telemetric signal. A remote control may, for example, be provided in combination with an ambulatory medical device such as an implantable infusion device or an implantable stimulation device. Implantable infusion devices frequently include a housing, a medication reservoir, a catheter with a discharge end, a pump or other fluid transfer device that moves the medication from the reservoir to the discharge end of the catheter, a telemetric communication device and a therapeutic device. Implantable stimulation devices may include a housing, electrodes, a source of stimulation energy, a telemetric communication device and a therapeutic device. In either case, the controller may be configured to provide basal delivery of medication or stimulation energy in accordance with instructions provided by the physician. The controller may also be configured to provide bolus delivery in response to an instruction from the patient. Such a "bolus" instruction, which can be communicated to the implantable device by way of a remote control, may come in response to a high glucose level measurement in the case of a diabetic patient, an increase in pain level in the case of a pain management patient, or some other symptom that is associated with the particular medical condition that the therapeutic device is intended to treat.

The present inventors have determined that one issue associated with the use of remote controls in medical systems, especially remote controls carried by patients, is inadvertent actuation and the resulting undesirable delivery of medication, stimulation energy, or other therapies. More specifically, the present inventors have determined that the buttons on the remote control in a conventional ambulatory medical device system may be inadvertently pressed while the remote control is being carried in the patient's hand, pocket, purse or the like, or is being stored in a location where it is at risk of being inadvertently contacted. In addition to the user simply unintentionally pressing the button, keys carried within a pocket or purse can, for example, also press a button. In other situations, such as when a remote control is placed on a bed or chair, the user may sit on the remote and cause buttons to be pressed.

SUMMARY OF THE INVENTIONS

A remote control in accordance with one invention includes a button, apparatus for communicating with a medical device in response to pressing of the button, and apparatus for preventing inadvertent communication with the medical device.

A remote control in accordance with another invention includes a button, a button control element movable between a first position where the button is substantially prevented from being pressed and a second position where the button is not substantially prevented being pressed, and apparatus for communicating with a medical device in response to the button being pressed.

A remote control in accordance with another invention includes a button, a button control element, a communication device adapted to transmit a signal, and a controller adapted to prevent signal transmission by the communication device unless the button control element has been actuated.

A remote control in accordance with another invention includes a single button, apparatus for maintaining the remote control in a locked state in which a signal will not be transmitted to a medical device in response to the single button being pressed, and apparatus for unlocking the remote control in response to a predetermined sequence of presses of the single button.

A remote control in accordance with another invention includes a communication device, an actuator operably connected to the communication device, and a depressible member, movable between a first position where the depressible member is prevented from being depressed and a second position where the depressible member is substantially aligned with the actuator and is not prevented being depressed.

A method of operating a remote control in accordance with another invention includes the step of maintaining the remote control in locked state where pressing the button will not result in signal transmission to a medical device and the step of unlocking the remote control when the user takes an action that demonstrates an intent to transmit a signal.

Such remote controls and methods, which are particularly advantageous because they greatly reduce the likelihood of inadvertent actuation, may also be part of medical systems that include a remote control and a therapeutic device. For example, the remote controls may be part of an ambulatory medical device system that includes an ambulatory medical device such an implantable infusion device or implantable stimulation device.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

Figure 1:
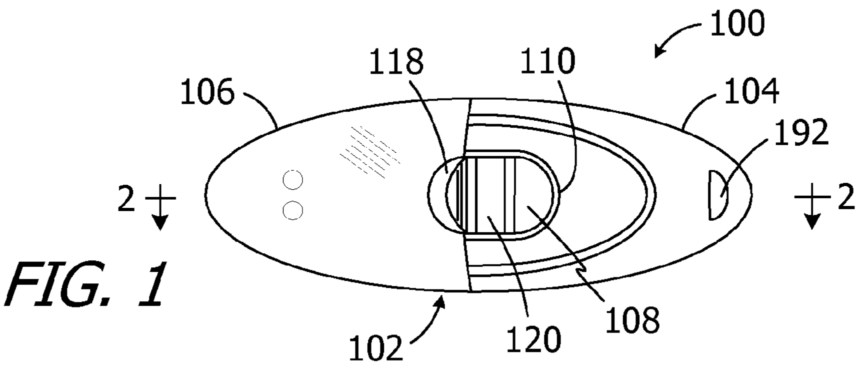
FIG. 1 is a plan view of a remote control in a locked state in accordance with one embodiment of a present invention.

The following is a detailed description of the best presently known modes of carrying out the inventions. This description is not to be taken in a limiting sense, but is made merely for the purpose of illustrating the general principles of the inventions. The detailed description is organized as follows:

I. Exemplary Remote Controls

II. Exemplary Ambulatory Medical Device Systems

The section titles and overall organization of the present detailed description are for the purpose of convenience only and are not intended to limit the present inventions.

The present remote controls have application in a wide variety of medical device systems. One example of such a system is an implantable infusion device system and the present inventions are discussed in the context of implantable infusion device systems. The present inventions are not, however, limited to implantable infusion device systems and are instead also applicable to other medical device systems that currently exist, or are yet to be developed. For example, the present inventions are applicable to other ambulatory medical device systems. Such systems include, but are not limited to, externally carried infusion pump systems, implantable pacemaker and/or defibrillator systems, implantable neural stimulator systems, and implantable and/or externally carried physiologic sensor systems.

I. Exemplary Remote Controls

One exemplary embodiment of a remote control in accordance with one of the present inventions is generally represented by reference numeral 100 in FIGS. 1-5. The exemplary remote control 100 includes a housing 102 and a button 104. The housing 102 carries a movable button control element 106 with a depressible member 108 that is positioned over the button 104. As discussed in greater detail below, the remote control 100 will generate a signal when the button 104 is pressed and, depending on its position, the button control element 106 will control the operation of the button by either preventing or allowing the button to be pressed.

Figure 2:
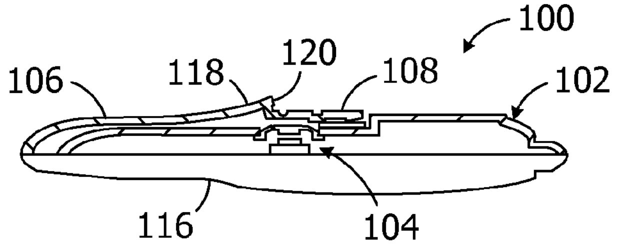
FIG. 2 is partial section view taken along line 2-2 in FIG. 1.

The exemplary remote control 100 is shown in the locked state, i.e. the state in which the button 104 may not be pressed, in FIGS. 1 and 2. More specifically, when the movable button control element 106 is in the position illustrated in FIGS. 1 and 2, the depressible member 108 will be aligned with a barrier 110 (FIG. 3) on the housing 102. The barrier 110, which may include abutments 112, prevents the depressible member 108 on the button control element 106 from being depressed, thereby preventing the button 104 from being pressed.

Figure 3:
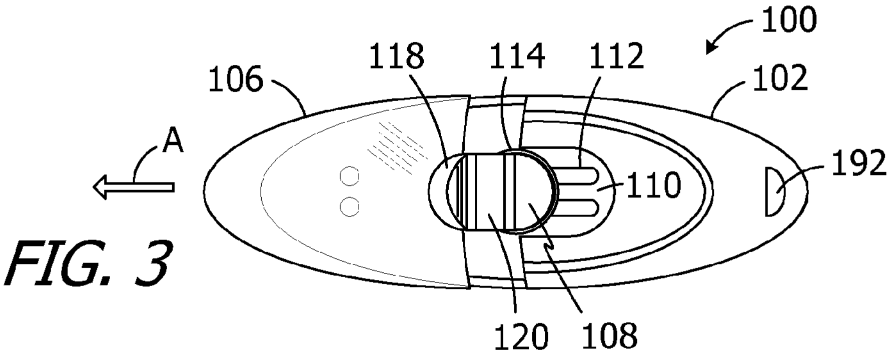
FIG. 3 is a plan view of the remote control illustrated in FIG. 1 in an unlocked state.
Figure 4:
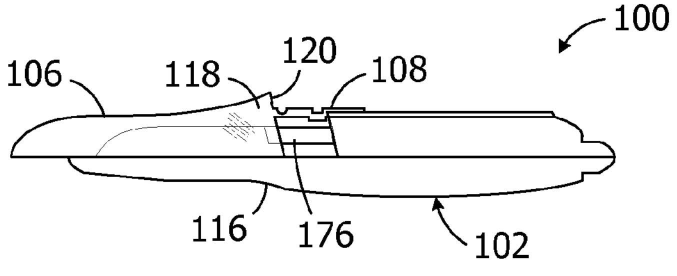
FIG. 4 is a side view of the remote control illustrated in FIG. 1 in an unlocked state.

The exemplary remote control 100 may be adjusted to the unlocked state illustrated in FIGS. 3 and 4, i.e. the state in which the button 104 may be pressed, by moving the button control element 106 in the direction of arrow A until the depressible member 108 is no longer aligned with the barrier 110 and is instead aligned with a housing aperture 114 that is adjacent to the barrier. To that end, the housing 102 in the exemplary embodiment includes a surface 116 that is shaped to receive the user's forefinger and the button control element 106 includes a raised area 118 that combines with the depressible member 108 to form a region that is shaped to receive the user's thumb. This configuration allows the user to easily hold the remote control 100 between his or her thumb and forefinger and slide the button control element 106 with the thumb. The depressible member 108 and raised area 118 also include ridges 120 which prevent the user's thumb from slipping. Once the button control element 106 has reached the unlocked position illustrated in FIGS. 3 and 4, the user will be able to press the button 104 by moving the depressible member 108 in the direction indicated by arrow B in FIG. 5. This may be easily accomplished by simply pressing downwardly with the thumb.

The housing 102 and button control element 106 perform the advantageous function of preventing inadvertent communication between the exemplary remote control 100 and the associated medical device by preventing the button 104 from being pressed unless the user has demonstrated his/her intent to press the button. Such intent is demonstrated, in the context of the exemplary remote control 100, by sliding the button control element 106 from the locked position (FIGS. 1 and 2) to the unlocked position (FIGS. 3 and 4) prior to pressing the button 104.

Figure 5:
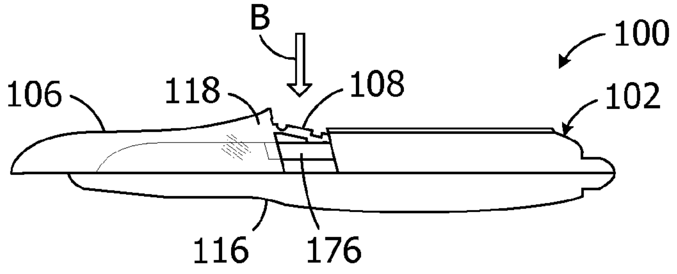
FIG. 5 is a side view of the remote control illustrated in FIG. 1 in an unlocked state and actuated state.

There are a variety of structural configurations that would allow a remote control to move from a locked state to an unlocked state in the manner illustrated in FIGS. 1-4, and then be actuated in the manner illustrated in FIG. 5. One example of such a configuration is described below with reference to FIGS. 6-13.

Referring first to FIGS. 6-9, the exemplary housing 102 includes a bottom member 122 and a top member 124. The bottom member 122 has a main wall 126, an outer wall 128 that extends around the perimeter of the main wall, and inner walls 130 and 132. The inner walls 130 and 132 define storage regions for a circuit board 134 and a battery 136. The circuit board 134 carries a controller 138, a communication device 140 (including an antenna), an actuator 142 with a movable element 144, and a pair of LEDs 146 (or other light emitting elements). The LEDs 146, which may be the same color or different colors (e.g. green and red), may be used to communicate various diagnostic issues (e.g. a low battery) as well as the other issues described below. The movable element 144 is aligned with the housing aperture 114 and, in the illustrated embodiment, the housing aperture is covered by a resilient cover 148 that keeps dirt and moisture out of the closed interior space within the housing 102. The actuator 142 may be, for example, a normally open switch that is biased to the open state and is closed in response to downward (in the illustrated orientation) movement of the movable element 144, as is discussed in greater detail below with reference to FIG. 13.

The exemplary button 104, which consists of the actuator 142 and the resilient cover 148, may be pressed by depressing the depressible member 108 when the remote control 100 is in the unlocked state (FIGS. 3-5). Specifically, the depressible member 108 will press the resilient cover 148 which, in turn, will press the movable element 144 of the actuator 142 and close the switch. In some alternative embodiments, the housing aperture 114 will be uncovered and the depressible member 108 will come into direct contact with the actuator 142. In either case, the controller 138 will instruct the communication device 140 to transmit a signal when the switch is closed. Additional information concerning functionality of the controller 138 as well as the other elements carried by the circuit board 134 is provided below in the context of FIGS. 41 and 42.

Figure 6:
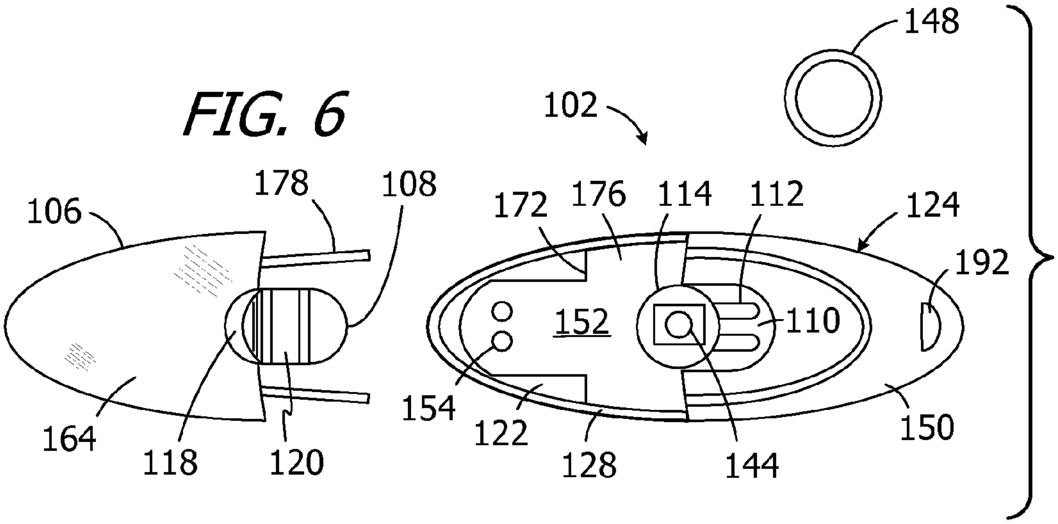
FIG. 6 is a partially exploded view of the remote control illustrated in FIG. 1.
Figure 7:
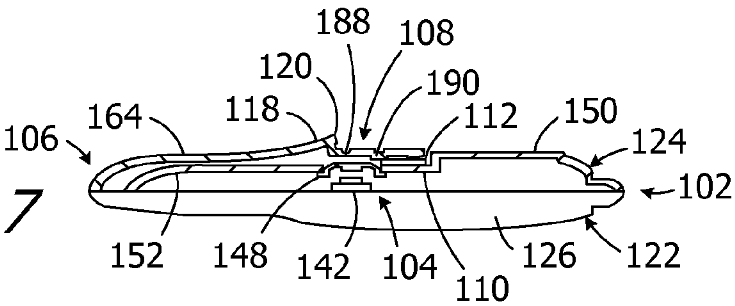
FIG. 7 is a side, partial section view of the remote control illustrated in FIG. 1 in a locked state.
Figure 8:
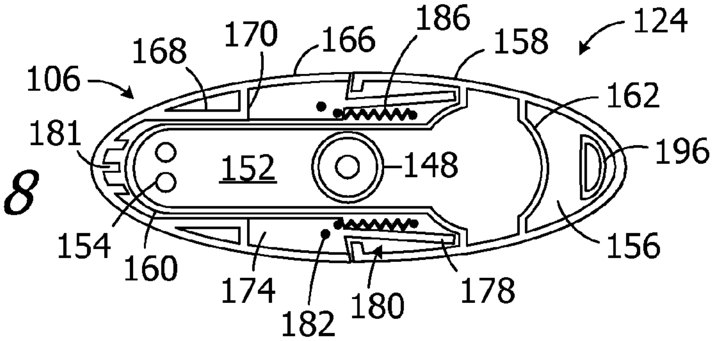
FIG. 8 is a plan view of the underside of an exemplary housing top member in a locked state.
Figure 9:
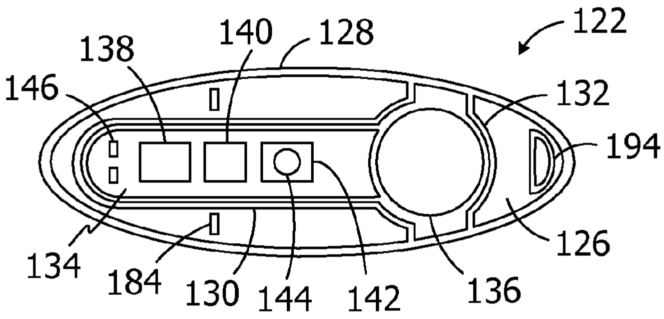
FIG. 9 is a plan view of an exemplary housing bottom member.
Figure 10:
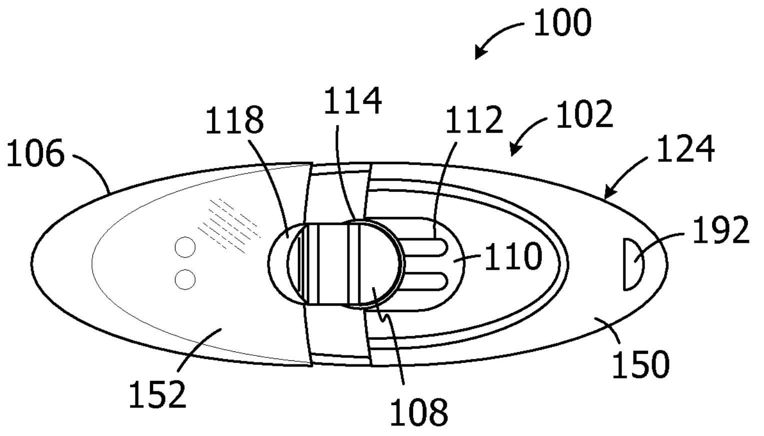
FIG. 10 is a plan view of the remote control illustrated in FIG. 1 in an unlocked state.
Figure 11:
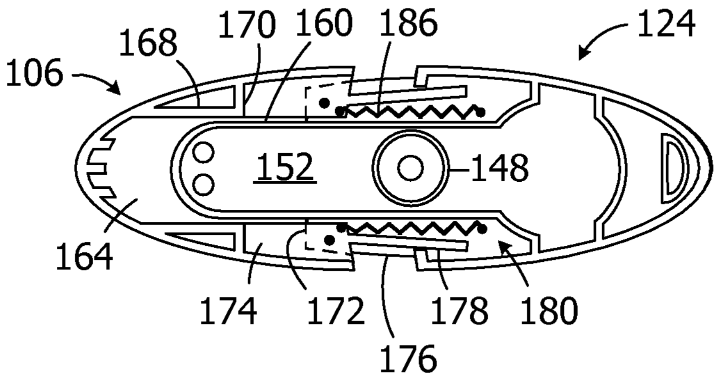
FIG. 11 is a plan view of the underside of the housing top member illustrated in FIG. 8 in an unlocked state.
Figure 12:
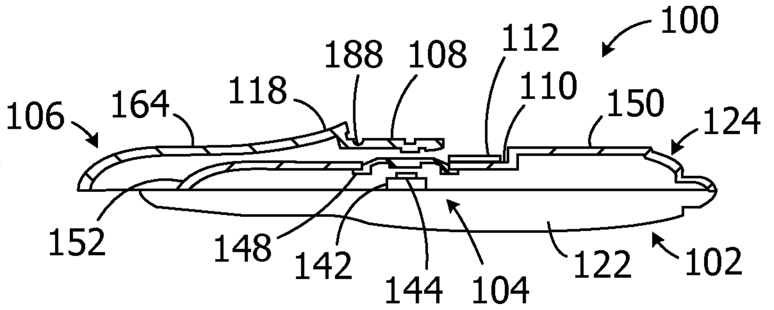
FIG. 12 is a side, partial section view of the remote control illustrated in FIG. 1 in an unlocked state.

As illustrated in FIGS. 6-8, the top member 124 of the exemplary housing 102 covers the bottom member 122, thereby defining a closed interior space, and also includes the housing aperture 114. The top member 124 may, for purposes of this description, be divided into a first section 150 that is generally aligned with the button control element 106, and a second section 152 that is located below the button control element. The barrier 110 and housing aperture 114 are part of the second section 152 and the barrier is located between the housing aperture and the first section 150. The second section 152 includes light apertures 154 that allow light from the LEDs 146 to pass through the housing 102. To that end, it should also be noted here that the button control element 106 in the illustrated embodiment is translucent. As such, light from the LEDs 146 that passes through the light apertures 154 will be visible to the user.

With respect to its other structural elements, the top member 124 illustrated in FIGS. 6-8 has a main wall 156 that forms the first and second sections 150 and 152, an outer wall 158, and inner walls 160 and 162. The outer and inner walls 128-132 of the bottom member 122 abut the outer and inner walls 158-162 of the top member 124. The bottom member 122 may also be provided with a plurality of holes (not shown), and the top member 124 may also be provided with a corresponding plurality of posts (not shown) that are configured to be interference fit into the holes to secure the top member to the bottom member.

Turning to the exemplary movable button control element 106, and referring to FIGS. 6-8, the button control element includes a main wall 164 and an outer wall 166. The button control element 106 is also configured to slide along the second section 152 of the housing top member 124. To that end, the button control element 106 is provided with a pair of longitudinally extending inner walls 168 that are in close proximity to, as well as parallel to, the two longitudinally extending portions of the top member inner wall 160. The button control element 106 also has transversely extending inner walls 170 that are positioned such that they abut transversely ending walls 172 (FIGS. 4-6) on the top member 124, thereby limiting the range of movement of the button control element relative to the housing 102. The button control element 106 also includes covers 174 (FIG. 8) that extend inwardly from the outer wall 166. The wide portions 176 (FIG. 6) of the top member second section 152 slide within the spaces defined by the covers 174 and the button control element main and outer walls 164 and 166. The button control element 106 is provided with a pair of guides 178 which slide within a corresponding pair of slots 180 (FIG. 8) that are located within the first section 150 of the housing top member 124. Finally, the button control element 106 includes a plurality of stop members 181 that engage the curved portion of the inner wall 160 on the housing top member 124.

The longitudinally extending portions of the top member inner wall 160, the movable portion inner walls 168, the covers 174, the top member wide portions 176, the guides 178 and slots 180 individually and collectively prevent the movable button control element 106 from sliding in any direction other than along the longitudinal axis of the housing 102. The orientation of the longitudinal axis is the same as the orientation of arrow A in FIG. 3. As a result, even in those instances where the user applies a pushing force to the button control element 106 which has a component that is transverse to longitudinal axis, the button control element will move in the longitudinal direction indicated by arrow A. The guides 178 also prevent debris from entering the housing 102 when the button control element 106 is in the unlocked position.

The covers 174 and the top member wide portion 176 also prevent the button control element 106 from being moved upwardly (in the orientation illustrated in FIG. 7) and pulled off the housing top member 124. Similarly, the alignment of the housing first section 150 with the button control element 106 (including the depressible member 108) prevents a fingernail or object from getting under, and lifting, the depressible member when the remote control 100 is in the locked state.

Forward movement of the button control element 106 relative to the housing 102, i.e. movement toward the unlocked position, is limited by a pair of pins 182 (FIG. 8) that extend downwardly from the covers 174 and engage a pair of stop members 184 (FIG. 9) on the housing bottom member 122 when the button control element reaches the unlocked position illustrated in FIG. 3. Rearward movement is limited by the transversely extending walls 170 and 172, as well as the stop members 181 and the curved portion of the inner wall 160.

The button control element 106 is biased to the locked position illustrated in FIGS. 1, 2, 7 and 8. Thus, unless the user is applying force to button control element 106 in the direction of arrow A (FIG. 3), the button control element will remain in the locked position and the depressible member 108 will remain on the barrier 110. Although the present inventions are not limited to any particular biasing arrangement, the exemplary remote control 100 includes a pair of tension springs 186. The tension springs 186 may be attached to the button control element 106 and to the housing top member 124. The tension springs 186 also help prevent the button control element 106 from being pulled off of the housing 102.

As noted above, the depressible member 108 is part of the button control element 106 and rests on the barrier abutments 112 when the exemplary remote control 100 is in the locked state. More specifically, in the illustrated embodiment, the depressible member 108 is secured to the remainder of the button control element 106 by a living hinge 188 (FIG. 7) and includes a pair of downwardly extending protrusions 190 that rest on the barrier abutments 112. The living hinge 188 allows the depressible member 108 to pivot from the position illustrated in FIG. 4 to the position illustrated in FIG. 5. The living hinge 188 also biases the depressible member 108 to the position illustrated in FIG. 4. The living hinge bias provides an additional level of safety in that simply overcoming the biasing force on the button control element 106 and moving the button control element to the unlocked position will not, in and of itself, result in the button 104 being pressed and a signal being generated. The user must also press the depressible member 108 while maintaining the button control element 106 in the unlocked position.

The manner in which some of the structural elements described above with reference to FIGS. 6-9 operate, as the exemplary remote control 100 is moved from the locked state to the unlocked state, are described below with reference to FIGS. 10-13. With respect to the interaction between the housing 102 and the button control element 106, the longitudinally extending inner walls 168 on the button control element slide along the longitudinally extending portions of the housing inner wall 160, and the transversely extending inner walls 170 on the button control element pull away from the transversely ending walls 172 on the housing. The spaces defined by the button control element main wall 164 and covers 174 will no longer completely enclose the wide portions 176 of the housing second section 152, and the button control element guides 178 will no longer be completely within the housing slots 180. The springs 186, which bias the button control element 106 to the locked position, will also stretch.

Figure 13:
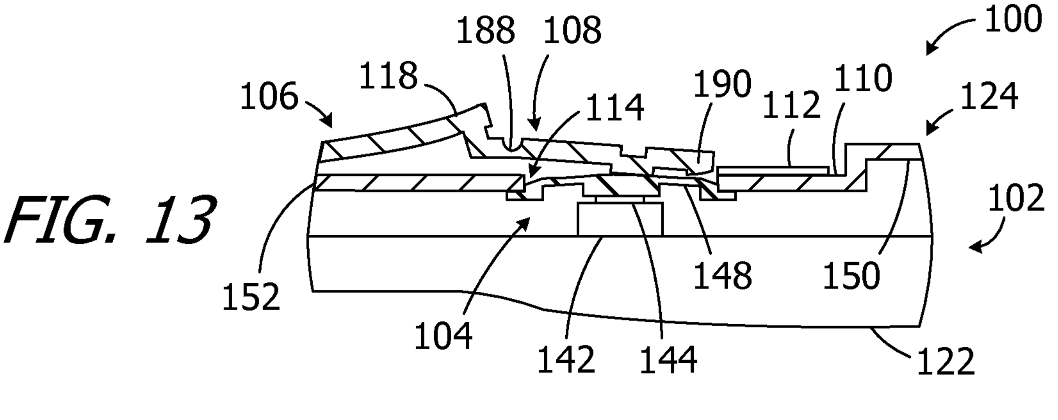
FIG. 13 is a side, partial section view of a portion the remote control illustrated in FIG. 1 in an unlocked and actuated state.

The exemplary remote control 100 is shown in the unlocked and actuated state (i.e. with the button 104 pressed) in FIG. 13. The depressible member 108 is aligned with the aperture 114 and pivoted about the living hinge 188 into contact with the resilient cover 148. As a result of the downward force applied by the depressible member 108, the resilient cover 148 is collapses and presses the movable element 144 on the actuator 142, thereby causing the remote control 100 to generate a signal.

The exemplary housing 102 is also provided with an opening 192 that allows the remote control 100 to be secured to, for example, a band of material and worn like a necklace or to a connector ring that facilitates connection to a key chain or a belt loop. The housing top and bottom members 122 and 124 may respectively include sealing walls 194 and 196 (FIGS. 8 and 9) that contact one and other and prevent dirt and moisture from entering the housing 102 by way of the opening 192.

Although the present inventions are not limited to any particular sizes, the exemplary remote control 100 may be sized such that it can be conveniently held between the thumb and forefinger and/or placed in the user's pocket. In one exemplary implementation, the remote control 100 is about 7.5 cm long, 3.5 cm wide and, at its thickest region, about 1.5 cm thick.

Figure 14:
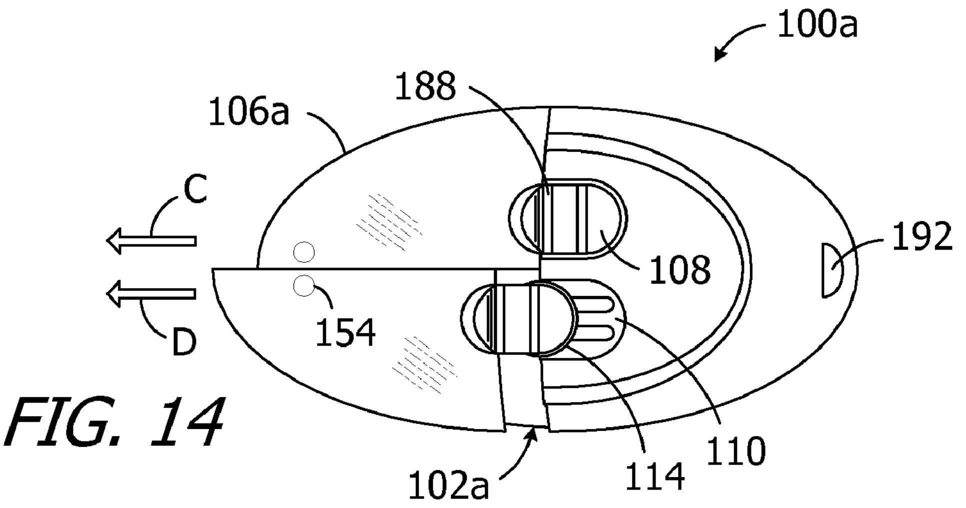
FIG. 14 is a plan view of a remote control with one portion in a locked state, and another portion in an unlocked state, in accordance with one embodiment of a present invention.

Another exemplary remote control is generally represented by reference numeral 100*a* in FIG. 14. Remote control 100*a* is substantially similar to remote control 100 and similar elements are represented by similar reference numerals. The remote control 100*a* also includes various similar elements that are not shown such as, for example, a circuit board with a controller and a communication device that operate in the manner described herein in the context of remote control 100. Unlike remote control 100, however, remote control 100*a* includes a pair of buttons (not shown) that may be individually pressed by the user. To that end, the exemplary housing 102*a* includes a pair of barriers 110 and a pair apertures 114. The remote control 100*a* is provided with a corresponding pair of independently operable button control elements 106*a*, each with a depressible member 108 and a living hinge 188. The exemplary button control elements 106*a* are mechanically keyed to one another such that they can slide relative to one another, in the directions indicated by arrows C and D, between the locked and unlocked positions illustrated in FIG. 14. Viewed as a single unit, the button control elements 106*a* are also secured to the housing 102*a*, and biased to the locked position, in essentially the same way that the button control element 106 is secured to the housing 102.

The housing 102*a* and button control elements 106*a* perform the advantageous function of preventing inadvertent communication between the exemplary remote control 100*a* and the associated medical device by preventing the buttons (not shown) from being pressed unless the user has demonstrated his/her intent to press a particular button. Such intent is demonstrated, in the context of the exemplary remote control 100*a*, by sliding the button control element 106*a* associated with that button from the locked position to the unlocked position.

Figure 15:
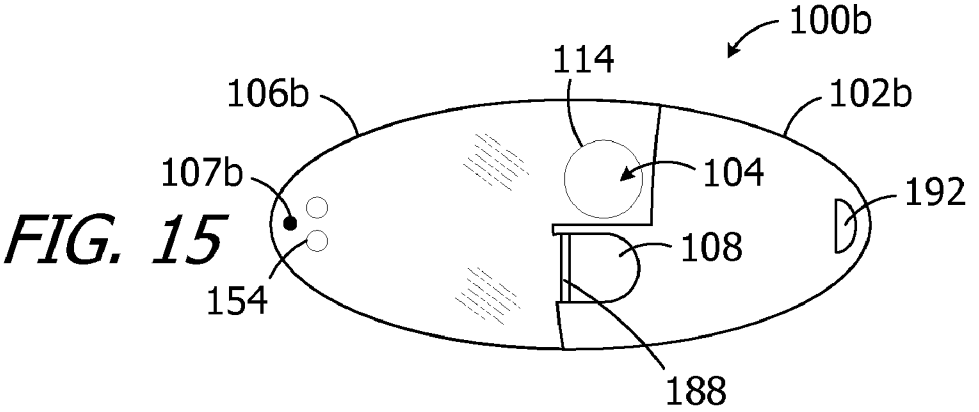
FIG. 15 is a plan view of a remote control in a locked state in accordance with one embodiment of a present invention.
Figure 16:
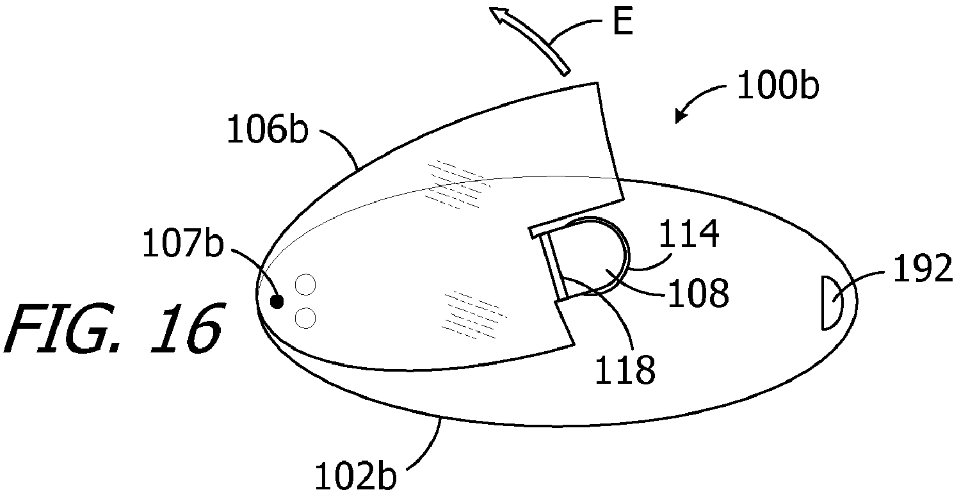
FIG. 16 is a plan view of the remote control illustrated in FIG. 15 in an unlocked state.

Still another exemplary remote control 100*b* is illustrated in FIGS. 15 and 16. Remote control 100*b* is substantially similar to remote control 100 and similar elements are represented by similar reference numerals. The remote control 100*b* also includes various similar elements that are not shown such as, for example, a circuit board with a controller and a communication device that operate in the manner described herein in the context of remote control 100. Unlike the remote control 100, which has a button control element 106 that slides longitudinally, the remote control **100*b* has a button control element 106*b* that pivots relative to the housing 102*b* in the direction indicated by arrow E. More specifically, the button control element 106*b* is pivotably secured to the housing 102*b* by a pin 107*b* and is biased to the locked position illustrated in FIG. 15. The button control element 106*b* includes a depressible member 108 and a living hinge 188. The housing aperture 114 and button 104 are offset from the depressible member 108 in a substantially transverse direction when the button control element 106*b* is in the locked position (FIG. 15). Here, the depressible member 108 rests on the top surface of the housing 102*b* and the button control element 106*b* covers the button 104. Rotation of the button control element 106*b* about the pin 107*b* to the unlocked position illustrated in FIG. 16 aligns the depressible member 108 with the housing aperture 114 and button 104. The depressible member 108 may then be depressed to cause the remote control 100*b* to generate a signal. It should also be noted that top surface of housing 102*b* and underside of the button control element 106*b* are substantially flat in order to facilitate the movement illustrated in FIGS. 15 and 16**.

The button control element **106*b* performs the advantageous function of preventing inadvertent communication between the exemplary remote control 100*b* and the associated medical device by preventing the button 104 from being pressed unless the user has demonstrated his/her intent to press the button. Such intent is demonstrated, in the context of the exemplary remote control 100*b*, by rotating the button control element 106*b* from the locked position (FIG. 15) to the unlocked position (FIG. 16**).

Figure 17:
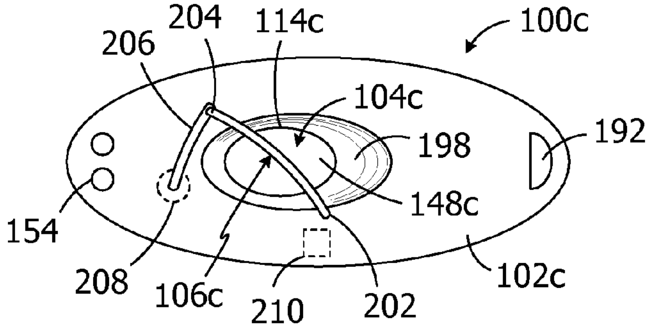
FIG. 17 is a plan view of a remote control in a locked state in accordance with one embodiment of a present invention.
Figure 18:
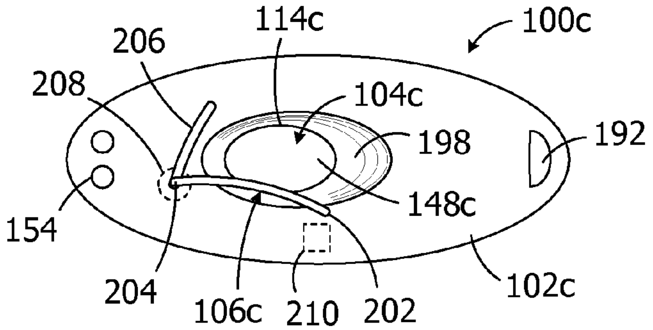
FIG. 18 is a plan view of the remote control illustrated in FIG. 17 in an unlocked state.

Yet another exemplary remote control is generally represented by reference numeral **100*c* in FIGS. 17 and 18. Remote control 100*c* is similar to remote control 100 and similar elements are represented by similar reference numerals. The remote control 100*c* also includes various similar elements that are not shown such as, for example, a circuit board with a controller and a communication device that, but for the differences described below, operate in the manner described herein in the context of remote control 100. Here, however, the housing 102*c* includes a recessed area 198 and the aperture 114*c* is located within the recessed area. A button 104*c*, which consists of a resilient cover 148*c* and an actuator (not shown), is associated with the aperture 114*c*. The remote control 100*c* also includes a button control element 106*c* that is movable between the locked position illustrated in FIG. 17, where it extends over the button, and the unlocked position illustrated in FIG. 18**, where it does not extend over the button.

The exemplary button control element **106*c* is a thin, wire-like structure that pivots about a pivot pin (not shown) associated with the pivot end 202. The free end 204 slides within a groove 206 formed in the surface of the housing 102*c*. The exemplary button control element 106*c* is also biased to the position illustrated FIG. 17**. The biasing force may, for example, be provided by a spring or other resilient device that is connected to pivot pin.

The controller and communication device may be configured such that the remote control **100*c* transmits a signal whenever the button 104*c* is pressed. The remote control 100*c* is, in the illustrated embodiment, configured to determine whether or not the button control element 106*c* is in the unlocked position illustrated in FIG. 18 and to prevent signal transmission unless the button control element is in the unlocked position. For example, a sensor 208, which senses when the button control element free end 204 has reached the unlocked position illustrated in FIG. 18 and sends an "unlock" signal to the controller 138 in response, may be provided. A Hall effect sensor is, in those instances where the button control element 106 is formed entirely or partially from metal, one suitable example of such a sensor. Alternatively, or in addition, the angular position of the pivot end 202 may be used to indicate when the button control element free end 204 has reached the position illustrated in FIG. 18. A switch 210, which is associated with the pivot pin and closes when the free end 204 has reached the position illustrated in FIG. 18, is one example of an angular position sensor that may be used in conjunction with the pivot pin. In either case, the controller 138 may, in turn, be configured to prevent the remote control 100*c* from generating a signal when the button 104*c*** is pressed unless the "unlock" signal from a sensor has been received.

Accordingly, inadvertent communication between the exemplary remote control **100*c* and the associated medical device may be accomplished by preventing transmission unless the user has demonstrated his/her intent to press the button. Such intent is demonstrated, in the context of the exemplary remote control 100*c*, by rotating the button control element 106*c* from the locked position (FIG. 17) to the unlocked position (FIG. 18). The inadvertent communication prevention function may be performed by the button control element 106*c* alone or, in some embodiments, by the button control element in combination with the controller 138 and sensors 208 and/or 210**.

Figures 19, 20, 21:
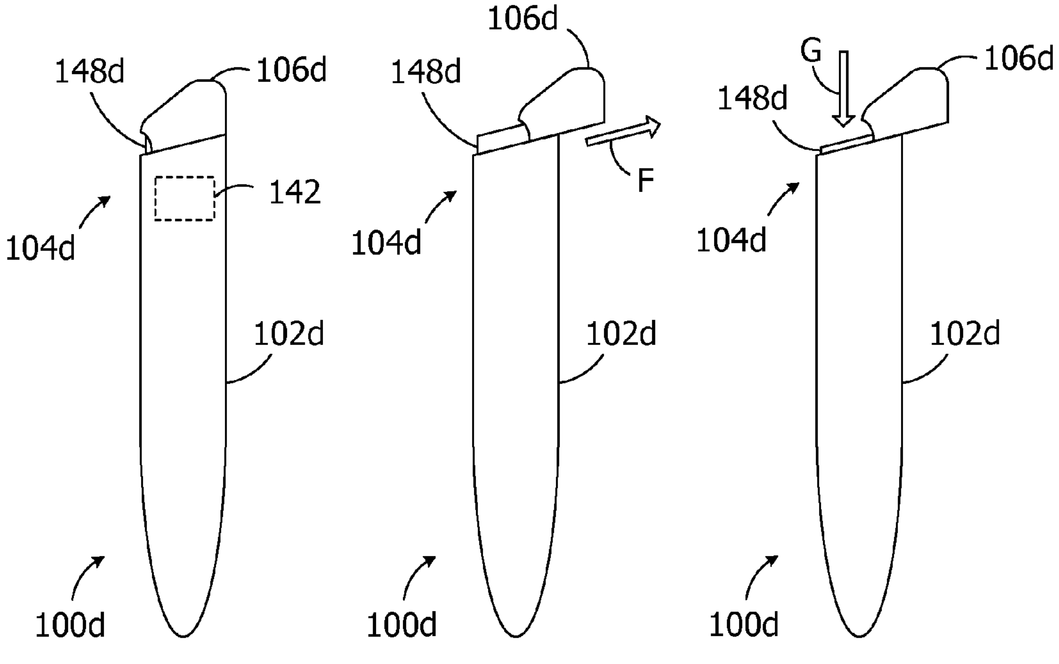
FIG. 19 is a side view of a remote control in a locked state in accordance with one embodiment of a present invention.
FIG. 20 is a side view of the remote control illustrated in FIG. 19 in an unlocked state.
FIG. 21 is a side view of the remote control illustrated in FIG. 19 in an unlocked and actuated state.

Turning to FIGS. 19-21, another exemplary remote control is generally represented by reference numeral **100*d*. Remote control 100*d* is substantially similar to remote control 100 and similar elements are represented by similar reference numerals. The remote control 100*d* also includes various similar elements that are not shown such as, for example, a circuit board with a controller and a communication device that operate in the manner described herein in the context of remote control 100. Unlike remote control 100, which has a housing 102 that is shaped to be held between the thumb and forefinger, remote control 100*d* includes a housing 102*d* with a long, thin shape that may be held between one or more fingers and the palm. A button 104*d*, which consists of an actuator 142 and a cover 148*d*, is positioned at one end of the housing 102*d***.

The exemplary remote control **100*d* also includes a movable button control element 106*d* that is carried by the housing 102*d* and is movable in the direction indicated by arrow F, which is generally transverse to the longitudinal axis of the housing. The exemplary remote control 100*d* is shown in the locked state, i.e. the state in which the button 104*d* may not be pressed because it is covered by the button control element 106*d*, in FIG. 19. Typically, the button control element 106*d* will be biased to the locked position illustrated in FIG. 19. The user may use his/her thumb to move the button control element 106*d* to the unlocked position shown in FIG. 20, thereby placing the remote control 100*d* in the unlocked state. The button 104*d* may then be pressed (FIG. 21) to cause the remote control 100*b*** to generate a signal.

The button control element **106*d* performs the advantageous function of preventing inadvertent communication between the exemplary remote control 100*d* and the associated medical device by preventing the button 104*d* from being pressed unless the user has demonstrated his/her intent to press the button. Such intent is demonstrated, in the context of the exemplary remote control 100*d*, by sliding the button control element 106*d* from the locked position (FIG. 19) to the unlocked position (FIG. 20**).

Figure 22:
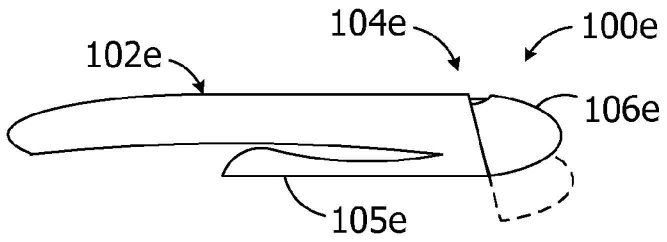
FIG. 22 is a side view of a remote control in a locked state in accordance with one embodiment of a present invention.

The exemplary remote control 100*e* illustrated in FIG. 22 is essentially identical to the remote control 100*d* illustrated in FIGS. 19-21. Here, however, the shape of the housing 102*e* and the slidable button control element 106*e* are such that the remote control 100*e* has an overall shape similar to that of a conventional pen. To that end, the housing 102*e* also includes a clip 105*e*. The exemplary remote control 100*e* may be moved from the locked state (solid lines) to the unlocked state (dashed lines) by sliding the button control element 106*e* relative to the housing 102*e*. Here too, this may be accomplished using the thumb. The user will then be able to generate a signal by pressing the button 104*e*.

Figure 26:
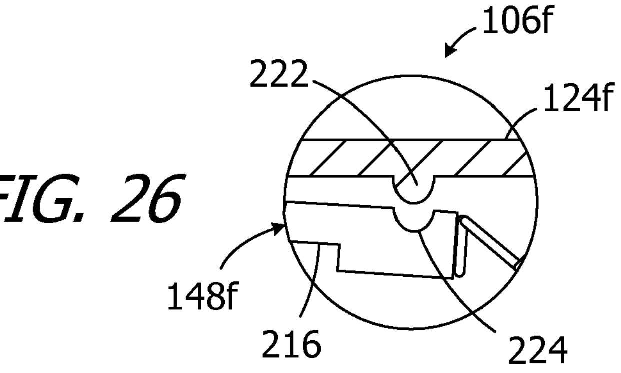
FIG. 26 is a section view of a portion of the remote control illustrated in FIG. 23 in the unlocked state.
Figure 27:
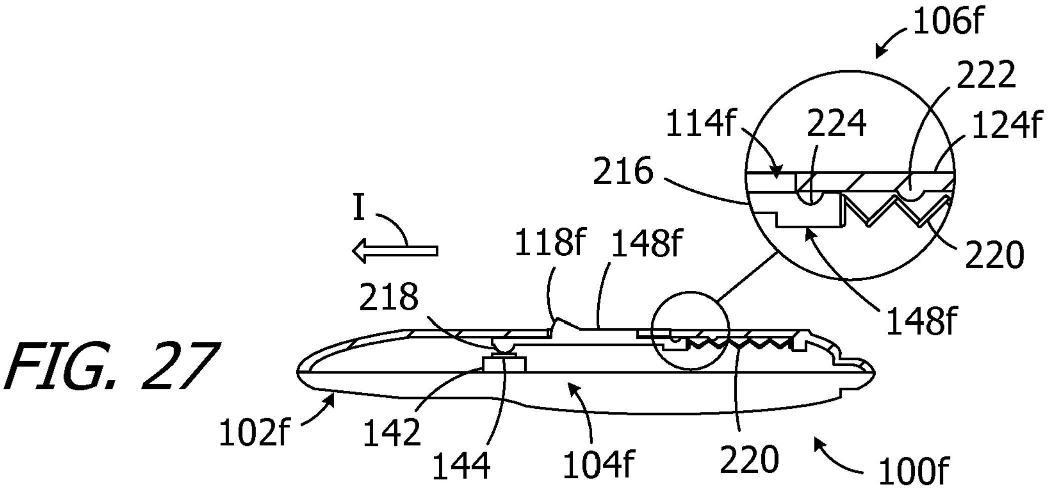
FIG. 27 is a partial section view of the remote control illustrated in FIG. 23 in an unlocked and actuated state.

Another exemplary remote control is generally represented by reference numeral 100*f* in FIGS. 23-27. Remote control 100*f* is substantially similar to remote control 100 and similar elements are represented by similar reference numerals. The remote control 100*f* also includes various similar elements that are not shown such as, for example, a circuit board with a controller and a communication device that operate in the manner described herein in the context of remote control 100. Unlike remote control 100, where the button 104 is pressed by pressing the resilient cover 148 inwardly relative to the housing 102, the button 104*f* on the exemplary remote control 100*f* is pressed by moving a slidable cover 148*f* longitudinally. To that end, the lateral edges of the slidable cover 148*f* may be carried by supports (not shown) that hold the slidable cover against the inner surface of the housing top member 124*f*. The slidable cover 148*f* also includes an upper portion 214 that is shorter (in the longitudinal direction) than the housing aperture 114*f*, and a lower portion 216 that is longer and wider than the housing aperture. The slidable cover upper portion 214 has a raised area 118 to engage the user's thumb, while the lower portion has a protrusion 218 that will contact the movable element 144 on the actuator 142 when the button 104*f* is pressed (FIG. 27). A tension spring 220 biases the slidable cover 148*f* to the non-pressed and locked position illustrated in FIGS. 23 and 24.

The remote control 100*f* is also provided with a button control element 106*f* that consists of a protrusion and a detent that is configured to receive the protrusion. As illustrated for example in FIG. 24, and although the locations of the detent and protrusion may be reversed, a protrusion 222 extends inwardly from the inner surface of the housing top member 124*f* and a detent 224 is formed in the slidable cover lower portion 216. The protrusion 222 rests in the detent 224, thereby preventing the button 104*f* from being pressed (i.e. by sliding the slidable cover 148*f*), when the remote control 100*f* is in the locked state illustrated in FIGS. 23 and 24. The remote control 100*f* may be unlocked by moving the slidable cover 148*f* in the direction indicated by arrow H. The downward movement (in the illustrated orientation) of the slidable cover 148*f* causes the detent 224 to move away from the protrusion 222, thereby unlocking the remote control 100*f*, as is illustrated in FIG. 26. Prior to ceasing the application of the downward force, the button 104*f* may be pressed by sliding the slidable cover 148*f* in the direction of arrow I to the position illustrated in FIG. 27 until the protrusion 218 engages the movable element 144 on the actuator 142. The spring 220 will return the slidable cover 148*f* to the locked position illustrated in FIGS. 23 and 24 when the button 104*f* is released.

Figure 23:
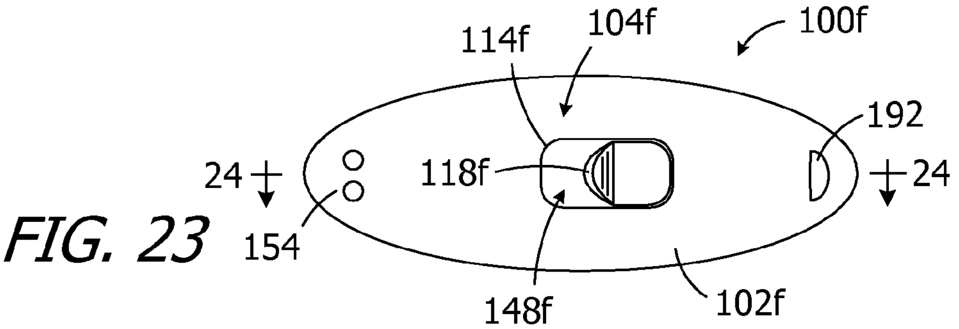
FIG. 23 is a plan view of a remote control in a locked state in accordance with one embodiment of a present invention.
Figure 24:
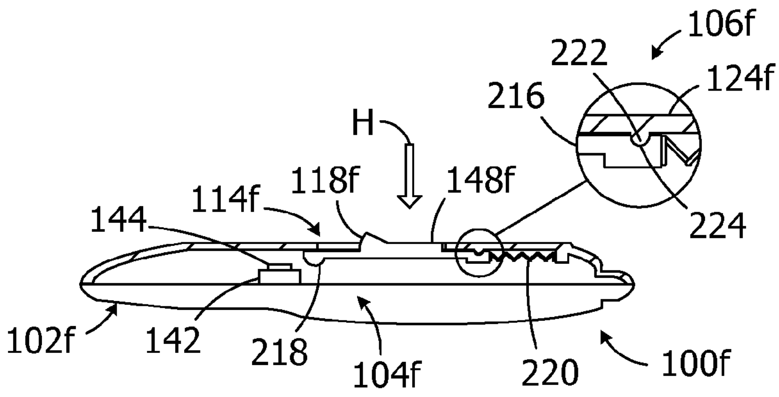
FIG. 24 is partial section view taken along line 24-24 in FIG. 23.
Figure 25:
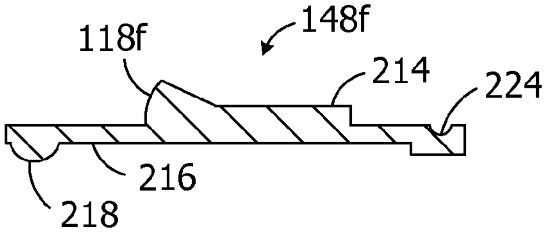
FIG. 25 is a section view of a portion of the remote control illustrated in FIG. 23.

It should be noted here that the aforementioned supports for the slidable cover 148*f* are configured to allow the slidable cover to move slightly inwardly from the locked position illustrated in FIGS. 23 and 24, to the unlocked position illustrated in FIG. 26, and back. Additionally, the housing aperture 114*f* and slidable cover upper portion 214 are sized and arranged such that the longitudinal ends of the housing aperture will contact the upper portion, and prevent further movement thereof, when the slidable cover 148*f* reaches the pressed position (FIG. 27) and the locked position (FIGS. 23 and 24).

The button control element 106*f* performs the advantageous function of preventing inadvertent communication between the exemplary remote control 100*f* and the associated medical device by preventing the button 104*f* from being pressed unless the user has demonstrated his/her intent to press the button. Such intent is demonstrated, in the context of the exemplary remote control 100*f*, by moving the slidable cover 148*f* downwardly from the locked position (FIGS. 23 and 24) to the unlocked position (FIG. 26), prior to pressing the button 104*f* by sliding it longitudinally.

Yet another exemplary remote control is generally represented by reference numeral 100*g* in FIGS. 28-31. Remote control 100*g* is substantially similar to remote controls 100 and 100*c* and similar elements are represented by similar reference numerals. The remote control 100*g* also includes various similar elements that are not shown such as, for example, a circuit board with a controller 138 and a communication device 140 that, but for the differences described below, operate in the manner described herein in the context of remote controls 100 and 100*c*. For example, remote control 100*g* includes a housing 102*g* with an opening 114*g*1 and an indentation 198 in the housing top member 124*g*, and a button 104*g* that is associated with opening. The button 104*g* includes a resilient cover 148*g*1 and an actuator 142 (FIG. 31), and the remote control 100*g* will transmit a signal if the button 104*g* is pressed when the remote control is in an unlocked state. Here, however, the button control element 106*g* does not cover the button 104*g* and is instead associated with the side of the housing 102*g* opposite the button 104*g*.

Figure 31:
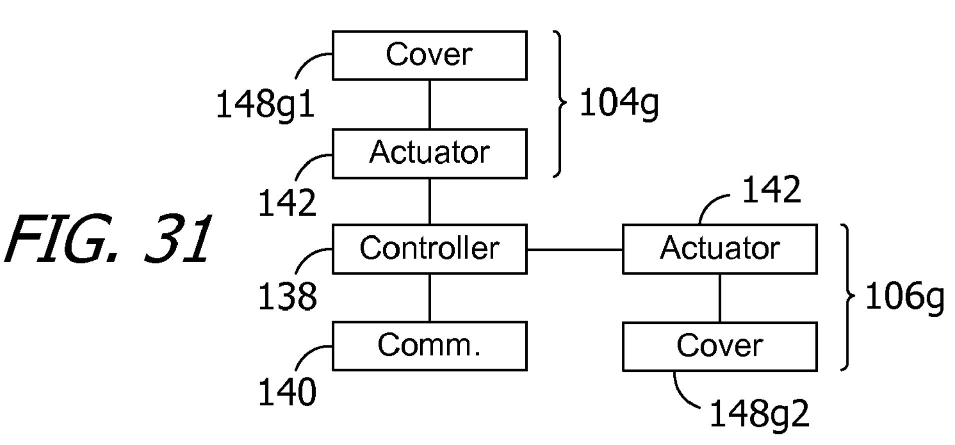
FIG. 31 is a block diagram showing certain aspects of the remote control illustrated in FIG. 28.

More specifically, the button control element 106*g* in the exemplary embodiment is in the form of a button, with a resilient cover 148*g*2 and an actuator 142 (FIG. 31), that is associated with an opening 114*g*2 on the housing bottom member 122*g*. The actuators of the button 104*g* and the button control element 106*g* are connected to the controller 138 (FIG. 31). During use, the controller 138 will not instruct the communication device 140 to transmit a signal in response to the user pressing button 104*g* unless the user also presses the button control element 106*g*, thereby unlocking the remote control 100*g*. The requisite pressing of button control element 106*g* may either be just prior to (e.g. within 1-5 seconds), or concurrent with, the pressing of button 104*g*. Thus, although the button control element 106*g* does not cover or physically prevent the button 104*g* from being pressed, the button control element is used to selectively prevent and allow the transmission of the signal associated with the button 104*g*.

Figure 28:
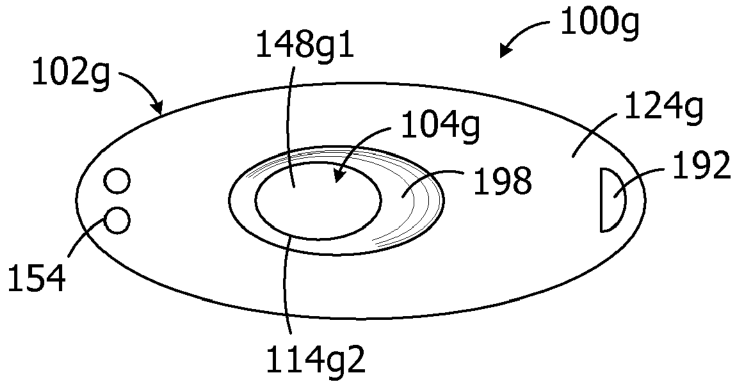
FIG. 28 is a top plan view of a remote control in accordance with one embodiment of a present invention.
Figure 29:
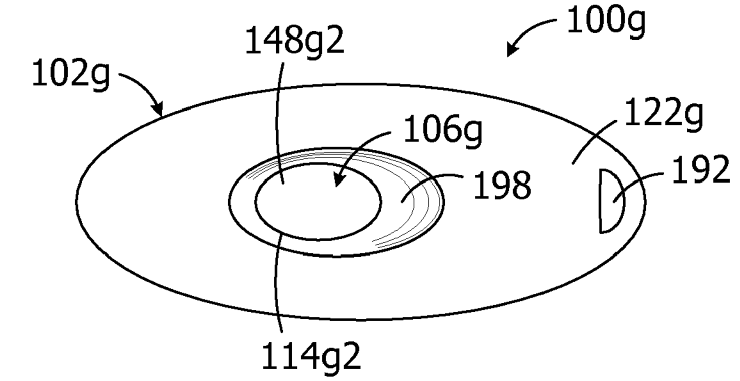
FIG. 29 is a bottom plan view of the remote control illustrated in FIG. 28.
Figure 30:
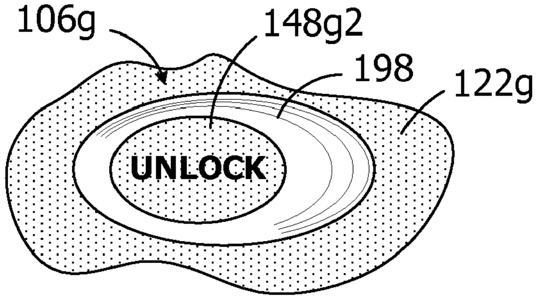
FIG. 30 is an enlarged view of a portion of the remote control illustrated in FIG. 28.

The exemplary remote control 100*g* may also be provided with tactile and/or visible indicia that distinguishes one button from the other. Referring more specifically to FIGS. 28 and 30, in the illustrated embodiment, the housing top member 124*g* and resilient cover 148*g*1 have smooth surfaces, while housing bottom member 122*g* and the resilient cover 148*g*2 are provided with roughened exterior surfaces. The top-bottom, rough-smooth aspect of the exemplary remote control may also be reversed. The resilient cover 148*g*2 also has the word "UNLOCK" thereon.

The button control element 106*g* and controller 138 perform the advantageous function of preventing inadvertent communication between the exemplary remote control 100*g* and the associated medical device by preventing the button 104*g* from causing a signal to be sent unless the user has demonstrated his/her intent to press the button. Such intent is demonstrated, in the context of the exemplary remote control 100*g*, by pressing the button control element 106*g*.

Figure 32:
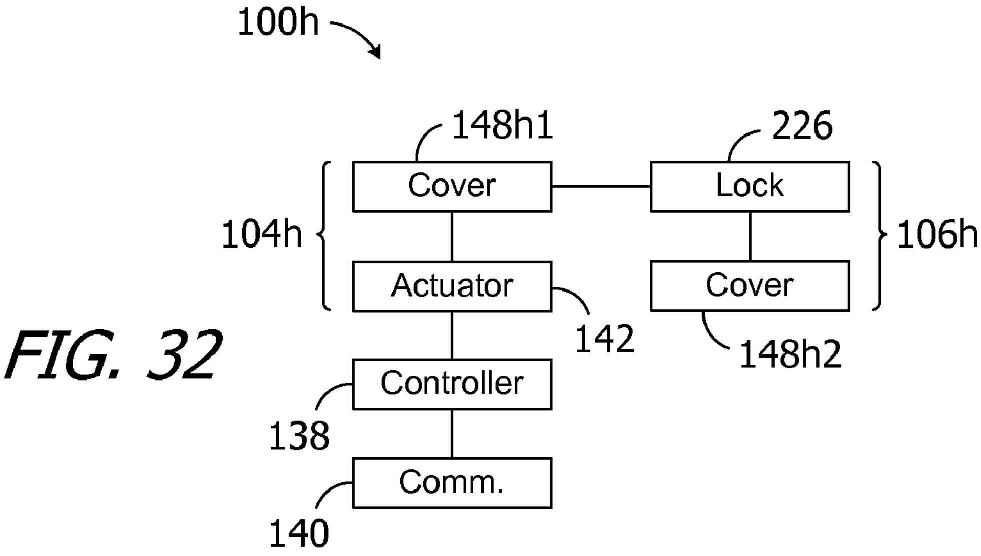
FIG. 32 is a block diagram showing certain aspects of a remote control in accordance with one embodiment of a present invention.

Another exemplary remote control is generally represented by reference numeral 100*h* in FIG. 32. Viewed from the exterior, remote control 100*h* is identical to the remote control 100*g* illustrated in FIGS. 28-30. The buttons 104*h* and button control element 106*h*, for example, have covers 148*h*1 and 148*h*2 that are on opposite sides of the housing. Here, however, the button control element 106*h* does not include an actuator that is connected to the controller 138 and the covers 148*h*1 and 148*h*2 are rigid. The button control element 106*h* has a mechanical button lock 226 that is operably connected to the cover 148*h*2 and to the button 104*h*. The mechanical lock 226 will typically be biased to the locked state where a portion of the lock is positioned so as to prevent the cover 148*h*1 from being pressed. The mechanical lock 226 may be unlocked by pressing the cover 148*h*2, thereby moving the aforementioned portion of the lock and allowing the first button 104*h*1 to be pressed and a signal to be transmitted.

The button control element 106*h* performs the advantageous function of preventing inadvertent communication between the exemplary remote control 100*h* and the associated medical device by preventing the button 104*h*1 from being pressed unless the user has demonstrated his/her intent to press the button. Such intent is demonstrated, in the context of the exemplary remote control 100*h*, by pressing the button 104*h*2.

Figure 33:
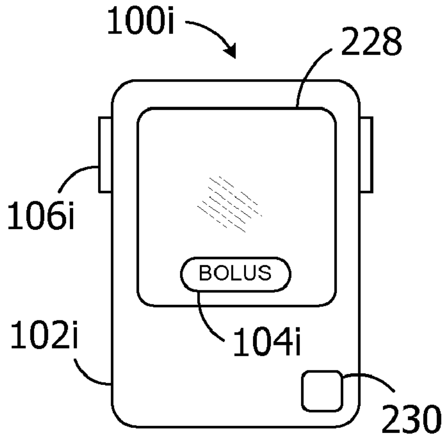
FIG. 33 is a plan view of a remote control in accordance with one embodiment of a present invention.

It should be noted here that, in the context of the present inventions, buttons are not limited to cover and actuator type devices employed in the exemplary embodiments described above. As illustrated for example in FIG. 33, the exemplary remote control 100*i* includes a housing 102*i* and a touch screen 228. A controller and a communication device (not shown) are also provided. The touch screen 228 may be used to display one or more button configurations in order to allow the user to accomplish various tasks. At least one of the displayed buttons is a bolus delivery button 104*i*. The housing 102*i* may also be provided with one or more button control elements 106*i* (e.g. buttons), which are operably connected to the controller, and an power on/off button 230. In order to conserve power, the remote control 100*i* has a sleep mode where the touch screen 228 is turned off despite the power being turned on. The remote control 100*i* may be awoken by pressing one of the button control elements 106*i* or any portion of the touch screen 228.

Although the remote control 100*i* may be used to perform other functions when the button control elements 106*i* are not being pressed, the remote control 100*i* will not transmit a bolus delivery signal unless the button control elements are being pressed when the bolus delivery button 104*i* is pressed. Accordingly, when bolus delivery is desired, the user may hold the remote control 100*i* in one hand, press the button control elements 106*i* with the thumb and forefinger, and press the bolus delivery button 104*i* with the other hand using a finger or a stylus. If the button control elements 106*i* are not being pressed when the bolus delivery button 104*i* is pressed, the controller will not cause the communication device to transmit a signal, but may cause a message to be displayed on the touch screen 228 which indicates that the bolus delivery signal was not transmitted. The message may also remind the user that that the button control elements 106*i* must be pressed in combination with the bolus delivery button if he or she does, in fact, desire a bolus delivery.

Figure 34:
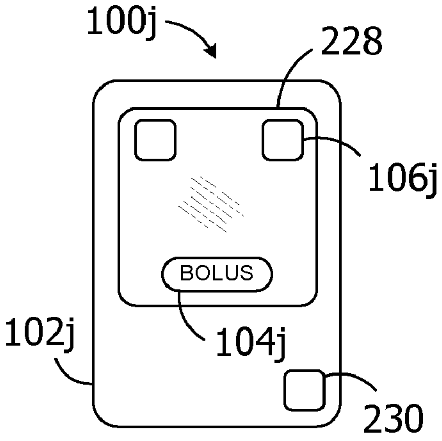
FIG. 34 is a plan view of a remote control in accordance with one embodiment of a present invention.

One or more button control elements may, alternatively, be provided on a touch screen. Turning to FIG. 34, the exemplary remote control 100*j* includes a housing 102*j*, a touch screen 228 that may be used to, among other things, display a bolus delivery button 104*j* and a pair of button control elements 106*j*, and a power on/off button 230. The remote control 100*j* also has a sleep mode. Although the remote control 100*j* may be used to perform other functions without the button control elements 106*j* being pressed, the remote control 100*j* will not transmit a bolus delivery signal unless the button control elements have been pressed just prior to (e.g. 1-5 seconds), or when, the bolus delivery button 104*j* is pressed. Accordingly, when bolus delivery is desired, the user may hold the remote control 100*j* in one hand, press the button control elements 106*j* with the other hand, and then the bolus delivery button 104*j* with the same hand. If the button control elements 106*j* have not been pressed prior to or concurrently with the bolus delivery button 104*j*, the controller will not cause the communication device to transmit a signal, but may cause a message to be displayed on the touch screen 228 which indicates that the bolus delivery signal was not transmitted. The message may also remind the user that that the button control elements must be pressed in combination with the bolus delivery button if he or she does, in fact, desire a bolus delivery.

The remote control controllers and the button control elements 106*i* and 106*j* perform the advantageous function of preventing inadvertent communication between the exemplary remote controls 100*i* and 100*j* and the associated medical devices by preventing the transmission of a signal unless the user has demonstrated his/her intent to press the bolus delivery buttons 104*i* and 104*j*. Such intent is demonstrated, in the context of the exemplary remote controls 100*i* and 100*j*, by pressing the button control elements 106*i* and 106*j*.

Figure 35:
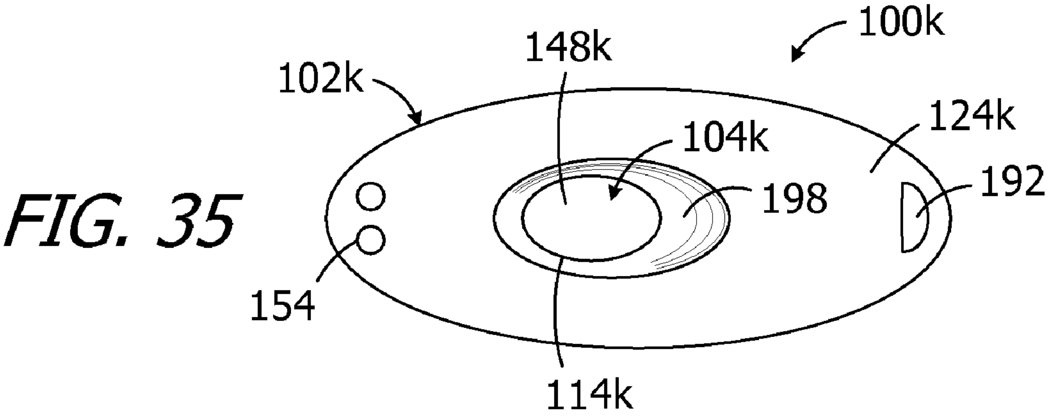
FIG. 35 is a top plan view of a remote control in accordance with one embodiment of a present invention.
Figure 36:
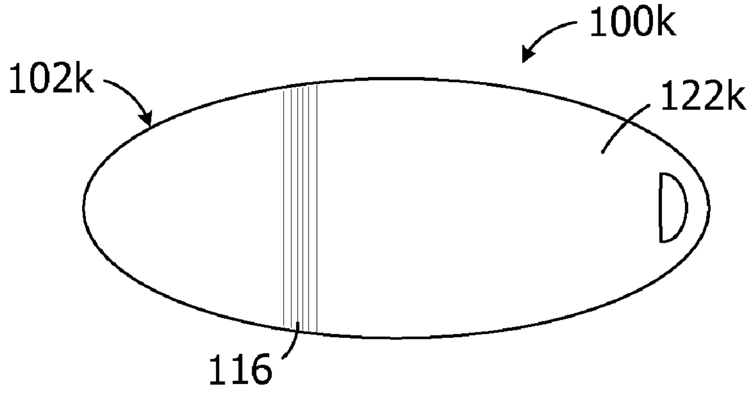
FIG. 36 is a bottom plan view of the remote control illustrated in FIG. 35.

Still another exemplary remote control is generally represented by reference numeral 100*k* in FIGS. 35 and 36. Remote control 100*k* is similar to remote controls 100 and 100*g* and similar elements are represented by similar reference numerals. The remote control 100*k* also includes various similar elements that are not shown such as, for example, a circuit board with a controller and a communication device that, but for the differences described below, operate in the manner described herein in the context of remote controls 100 and 100*g*. For example, the housing 102*k* includes a top member 124*k* with a recessed area 198 and an aperture 114*k*. A button 104*k*, which consists of a resilient cover 148*k* and an actuator (not shown), is associated with the aperture 114*k*. Here, however, the remote control 100*k* includes a single button 104*k* and there is no structure that physically or mechanically prevents the single button from being pressed.

As used herein, the phrase "a single button" means that the associated remote control has only one button. With respect to the exemplary remote control 100*k*, there are no other buttons on the housing top portion 124*k* (FIG. 35) and there are no buttons on the housing bottom portion 122*k*.

The button 104*k* may be used to cause the remote control 100*k* to transmit a signal in the manner described above. The button 104*k* may also be used as a button control element. More specifically, the controller may be configured such that the default state of the remote control 100*k* is the lock state and simply pressing the button 104*k* will not, in and of itself, result in the transmission of a signal. The remote control 100*k* must be unlocked using the button 104*k* prior to transmitting a signal. Once the remote control is unlocked, the user will have a brief period (e.g. about 3 seconds) to press the button 104*k* and transmit a signal. Once the unlocked period has expired or the signal has been transmitted, whichever occurs first, the remote control 100*k* will revert back to the locked state.

There are a variety of ways to use the button 104*k* to unlock the remote control 100*k*. There may, for example, be a predetermined unlocking sequence of button presses that would not be typically associated with an unintentional pressing of the button 104*k*. One such unlocking sequence is a prolonged press (e.g. 1-2 seconds) and release, followed immediately by a quick press and release, followed immediately by a prolonged press and release. The unlocking sequence may, alternatively, be a single prolonged press (e.g. 5 seconds). The LEDs 146 that are visible through the light apertures 154 may be used to indicate that the user is attempting to unlock the remote control 100*k* and/or that the remote control has been successfully unlocked and/or that the attempt to unlock the remote control was unsuccessful. Once the unlocking sequence has been received, the controller will cause the communication device to transit a signal in response to a pressing of the button 104*k* that is indicative of a bolus deliver request and occurs within the unlocked period. For example, one quick press and release, which is not followed by any additional presses, may be used to initiate a bolus delivery signal. The LEDs 146 may be used to indicate that a bolus delivery signal has been sent. Additionally, should any pressing of the button 104*k* other than an unlock sequence occur while the remote control 100*k* is in the locked state, the user will be made aware that no signal has been transmitted to the associated medical device though the use of, for example, the LEDs 146.

The button 104*k* and the controller perform the advantageous function of preventing inadvertent communication between the exemplary remote control 100*k* and the associated medical device by preventing the transmission of a signal unless the user has demonstrated his/her intent to press the button 104*k* for the purpose of transmitting a bolus delivery signal. Such intent is demonstrated, in the context of the exemplary remote control 100*k*, by imputing an unlocking sequence with the button 104*k*.

Figure 37:
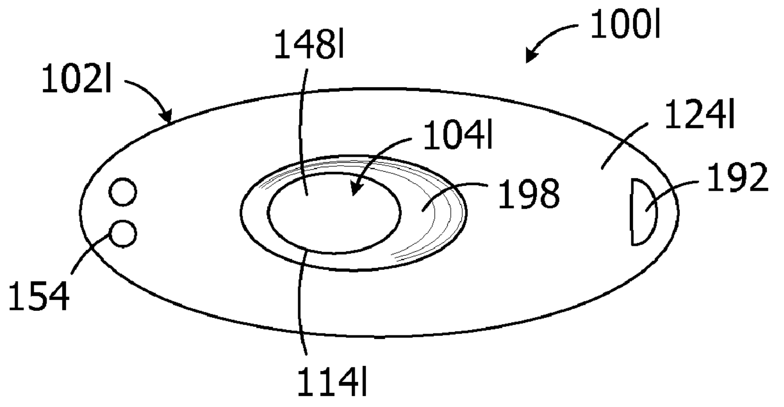
FIG. 37 is a top plan view of a remote control in accordance with one embodiment of a present invention.

Yet another exemplary remote control is generally represented by reference numeral 100*l* in FIG. 37. Remote control 100*l* is similar to remote control 100*k* and similar elements are represented by similar reference numerals. The remote control 100*l* also includes various similar elements that are not shown such as, for example, a circuit board with a controller and a communication device that operate in the manner described herein in the context of remote control 100*k*, but for the differences described below. For example, the housing 102*l* includes a top member 124*l* with a recessed area 198 and an aperture 114*l*. A button 104*l*, which consists of a resilient cover 148*l* and an actuator 142*l* (FIG. 39), is associated with the aperture 114*l*. The remote control 100*l* also includes LEDs 146 that may be used to communicate with the user in the manner described in the context of remote control 100*k*. Here, however, the remote control 100*l* does not include a battery (e.g. battery 136 in FIG. 9). Instead, as illustrated in FIGS. 38 and 39 power for the remote control 100*l* is provided by an energy generator 232 that converts movement of the remote control into energy and a capacitor 234 that may be used to store the energy generated by the energy generator 232.

Figure 38:
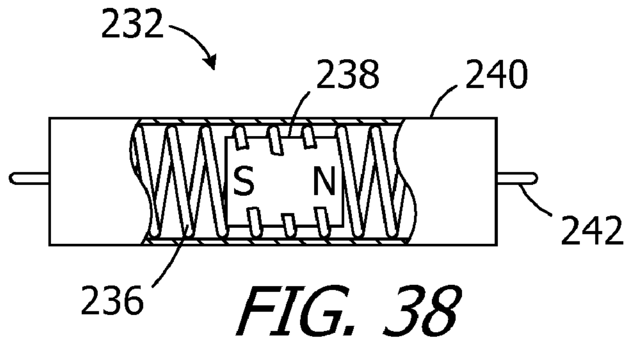
FIG. 38 is a cutaway view of an energy generator that may be used in combination with the remote control illustrated in FIG. 37.

Referring first to FIG. 38, the exemplary energy generator 232 includes one or more coils 236 (only one is shown for purposes of clarity), a permanent, relatively high strength magnet 238 that is positioned within the coil, and a non-conductive housing 240. Electrical contacts 242, which are connected to the coil 236, are positioned on the exterior of the housing 240. The magnet 238 will move back and forth within the coil 236 when the user shakes the remote control 100*l*. As the magnet 238 moves through the coil 236, a voltage is induced on the coil and a charge is compelled to move through wires that are connected to the generator contacts 242. The charge is stored by the capacitor 234.

Figure 39:
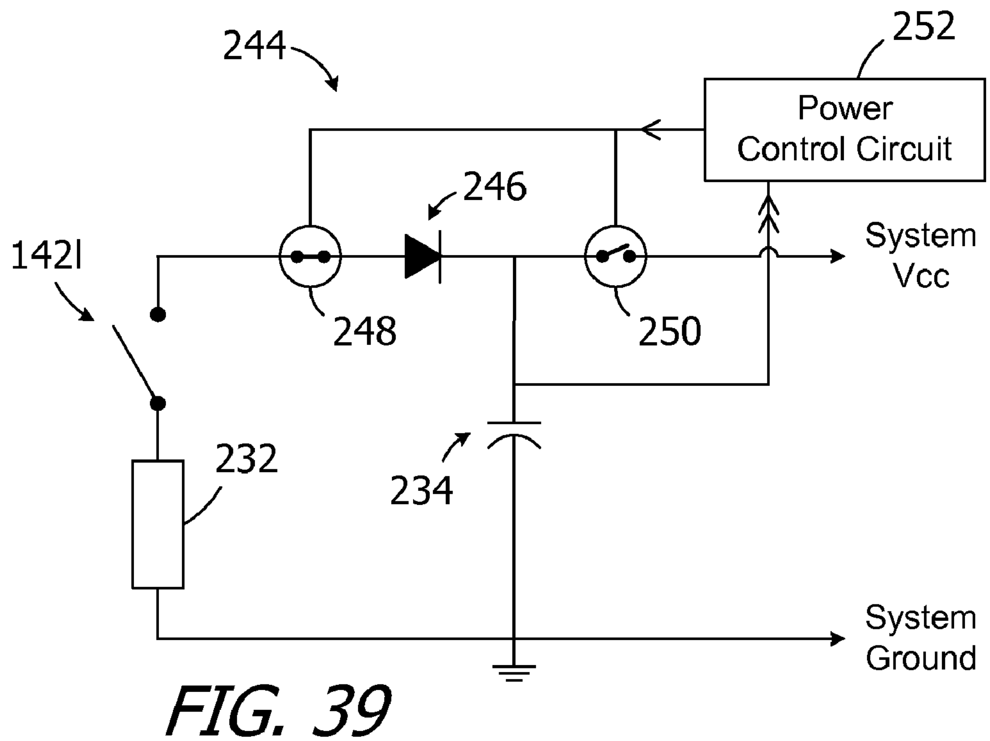
FIG. 39 is a circuit diagram in accordance with one embodiment of a present invention.

Turning to FIG. 39, the exemplary energy generator 232 and capacitor 234 are part of a power generation and control system 244, which also includes a diode 246, a normally closed switch 248, a normally open switch 250, and a power control circuit 252. The diode 246 is employed in the illustrated embodiment because the flow of current from the energy generator 232 alternates with the direction of movement of the magnet 238. The diode 246 allows charge to flow into the capacitor 234 when the magnet 238 is moving in one direction, and prevents charge from being removed from the capacitor when the magnet is moving in the other direction. The actuator 142*l* (i.e. a normally open switch) associated with the button 104*l* is also part of the power generation and control system 244. The circuit consisting of the energy generator 232 and the capacitor 234 is completed when the button 104*l* is pressed and the actuator 142*l* is closed. Accordingly, in order to charge the capacitor 234 with the energy generator 232, the user must press the button 104*l* while shaking the remote control 100*l*. Shaking and/or other motion that occurs when button 104*l* is not pressed is simply lost.

It should be noted here that the other operations of the button 104*l*, e.g., causing a bolus delivery signal to be transmitted, are not effected by the connection of the button to the power generation and control system 244.

The exemplary power generation and control system 244 operates as follows. As noted above, the capacitor 234 is charged by shaking the remote control 100*l* while the button 104*l* is being pressed. Power for the power control circuit 252 is also provided by the energy generator 232 at this time. When the charge on the capacitor 234 is sufficient to supply the system Vcc, the power control circuit 252 sends a signal that opens switch 248 and closes switch 250 in order to disconnect the energy generator 232 from the capacitor and connect the capacitor to the system Vcc. The user may, in some implementations, be provided with a visible and/or audible indication that the remote control 100*l* has been fully charged. The remote control 100*l* will boot up after the user releases the button 104*l*, and the remote control will operate in the manner described above, albeit with the capacitor 234 as the energy source instead of a battery. For example, the user may transmit a bolus delivery signal by pressing the button 104*l* after the remote control 100*l* has booted up.

The power control circuit 252, which is powered by the capacitor 234 once the remote control 100*l* has been charged, may also be configured to discharge any energy in the capacitor in predetermined situations in order to further prevent inadvertent signal transmission. For example, the power control circuit 252 may be configured to discharge any energy in the capacitor 234 after a predetermined period (e.g. two minutes) has elapsed subsequent to the shaking/charging, regardless of whether or not a signal has been transmitted. Alternatively, or in addition, the power control circuit 252 may be configured to discharge any energy in the capacitor 234 immediately after any signal has been transmitted, or only after a predetermined signal has been transmitted. For example, the power control circuit 252 may be configured to discharge any energy in the capacitor 234 immediately after a bolus delivery signal has been transmitted.

The button 104*l* and the power control circuit 252 perform the advantageous function of preventing inadvertent communication between the exemplary remote control 100*l* and the associated medical device by preventing the transmission of a signal unless the user has demonstrated his/her intent to press the button 104*l* for the purpose of transmitting a bolus delivery signal. Such intent is demonstrated, in the context of the exemplary remote control **100*l*, by shaking the remote control while pressing the button 104*l*** in order to charge the remote control.

Figure 40:
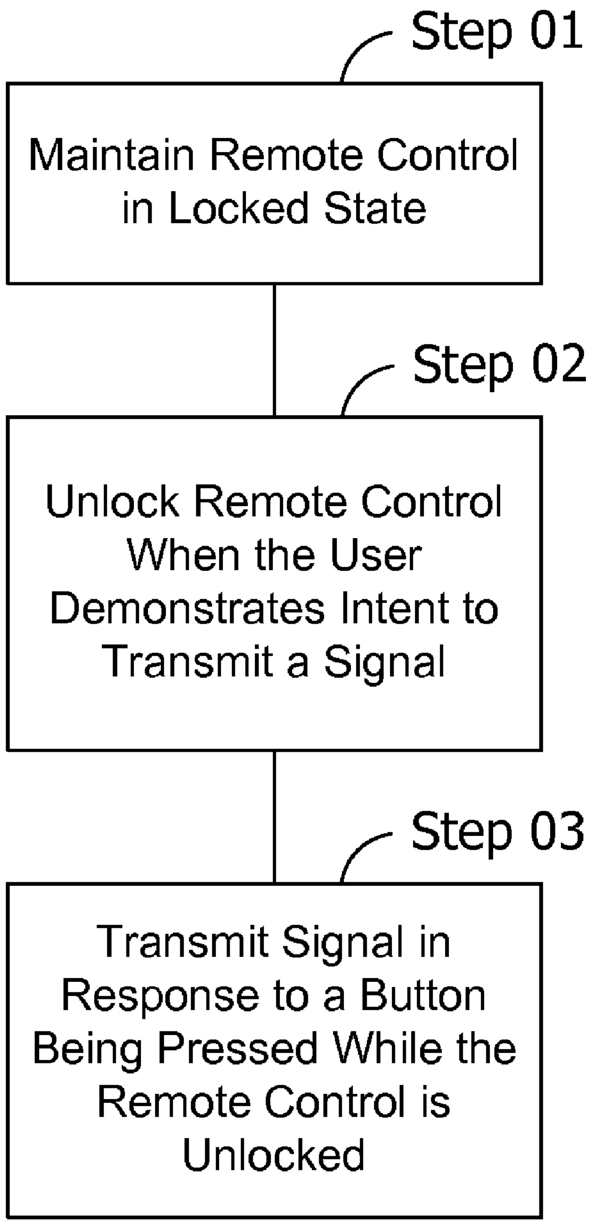
FIG. 40 is a flow chart in accordance with one embodiment of a present invention.

Turning to FIG. 40, the operational methodology of the exemplary remote controls **100-100*l*** may be summarized as follows.

The exemplary remote controls **100-100*l* are maintained in a default, locked state where the remote controls prevent signal transmission (Step 01). This may be accomplished, in the context of the illustrated embodiments, by (1) maintaining the button control element 106 in the position illustrated in FIGS. 1 and 2, thereby preventing the button 104 from being pressed; (2) maintaining the button control elements 106*a* in the position illustrated in the top half of FIG. 14, thereby preventing the associated buttons from being pressed; (3) maintaining the button control element 106*b* in the position illustrated in FIG. 15, thereby preventing the button 104 from being pressed; (4) maintaining the button control element 106*c* in the position illustrated in FIG. 17, thereby preventing the button 104*c* from being pressed; (5) maintaining the button control element 106*d* in the position illustrated in FIG. 19, thereby preventing the button 104*d* from being pressed; (6) maintaining the button control element 106*e* in the solid-line position illustrated in FIG. 22, thereby preventing the button 104*e* from being pressed; (7) maintaining the button control element 106*f* in the position illustrated in FIG. 24, thereby preventing the button 104*f* from being pressed; (8) blocking signal transmission that would otherwise result from the pressing of the buttons 104*g*, 104*i* and 104*j*; (9) maintaining the button control element 106*h* in the locked state, thereby preventing the button 104*h* from being pressed; (10) blocking signal transmission that would otherwise result from the pressing of the button 104*k*; and (11) withholding the energy necessary for the remote control 100*l*** to operate.

The exemplary remote controls **100-100*l* may be unlocked when the user takes an action that demonstrates his or her intent to transmit a signal (Step 02). This may be accomplished, in the context of the illustrated embodiments, by actuating the button control element by (1) moving the button control element 106 to the position illustrated in FIGS. 3 and 4, thereby unlocking the remote control 100; (2) moving the desired the button control element 106*a* to the position illustrated in the bottom half of FIG. 14, thereby unlocking the remote control 100*a* with respect to the corresponding button; (3) moving the button control element 106*b* to the position illustrated in FIG. 16, thereby unlocking the remote control 100*b*; (4) moving the button control element 106*c* to the position illustrated in FIG. 18, thereby unlocking the remote control 100*c*; (5) moving the button control element 106*d* to the position illustrated in FIG. 20, thereby unlocking the remote control 100*d*; (6) moving the button control element 106*e* in the dashed-line position illustrated in FIG. 22, thereby unlocking the remote control 100*e*; (7) pushing the cover 148*f* in the direction of arrow H (FIG. 24) so as to move dislodge one portion of the button control element 106*f* from the other (FIG. 26), thereby unlocking the remote control 100*f*; (8) pressing the button control elements 106*g*, 106*i* and 106*j*, thereby unlocking the remote controls 100*g*, 100*i* and 100*j*; (9) pressing the button control element 106*h*, thereby unlocking the remote control 100*h*; (10) imputing an unlocking sequence with the button 104*k*, thereby unlocking the remote control 100*k*; and (11) shaking the remote control 100*l* while pressing the button 104*l***. It should be noted here that, in the context of the present application, demonstrating the intent to transmit a signal is not simply turning a remote control on with an on/off button or waking up a remote control that is in a low power sleep mode.

Once unlocked, exemplary remote controls **100-100*l* may be used to transmit a signal (Step 03). This may be accomplished, in the context of the illustrated embodiments, by pressing the buttons 104-104*l***.

Additional steps may also be performed. For example, the exemplary remote controls **100-100*l* may also be returned to the locked state in response to user action or inaction. The return to the locked state may occur whether or not the remote controls are used to transmit a signal while unlocked. This may be accomplished, in the context of the illustrated embodiments, by (1) releasing the button control element 106 so that it will return the position illustrated in FIGS. 1 and 2; (2) releasing the desired the button control element 106*a* so that it will return to the position illustrated in the top half of FIG. 14; (3) releasing the button control element 106*b* so that it will return to the position illustrated in FIG. 15; (4) releasing the button control element 106*c* so that it will return to the position illustrated in FIG. 17; (5) releasing the button control element 106*d* so that it will return to the position illustrated in FIG. 19; (6) releasing the button control element 106*e* so that it will return in the solid-line position illustrated in FIG. 22; (7) releasing the cover 148*f* so that it will return to the position illustrated in FIGS. 23 and 24; (8) transmitting a signal by pressing the buttons 104*g*, 104*i* and 104*j* or not transmitting a signal within a predetermined period; (9) releasing the button control element 106*h*; (10) transmitting a signal by pressing the button 104*k* or not transmitting a signal within a predetermined period; and (11) transmitting a signal by pressing the button 104*l*** or not transmitting a signal within a predetermined period.

Finally, the remote controls **100-100*l* may also be unlocked in other ways (and in additional ways) for reasons other than transmitting a bolus delivery signal. For example, there may be a different predetermined unlocking sequence of button presses (e.g. three quick presses) that is used to unlock a remote control for purposes of mating a remote control with an implanted medical device. Such functionality is discussed in commonly assigned application Ser. No. 60/867,580, which is entitled "Method, Apparatus and System for Assigning Remote Control Device to Ambulatory Medical Device." For example, the exemplary remote control 100 may be unlocked for the purpose of simply pressing the button 104 by moving the button control element 106 to the unlocked position, and then unlocked for the purpose of mating the remote control with an implanted medical device by using the button 104** to input the unlocking sequence.

II. Exemplary Ambulatory Medical Device Systems

One example of an ambulatory medical device system in accordance with the present inventions is an implantable infusion device system. The implantable infusion device system may include any one of the remote controls **100-100*l* in combination with an implantable infusion device. The implantable infusion device system 10 illustrated in FIGS. 41 and 42, for example, includes a remote control 100 and an implantable infusion device 300**.

As noted above, the exemplary remote control 100 includes a battery or other power source 136, a controller 138, such as a microprocessor, microcontroller or other control circuitry, memory 139, an actuator 142 with a movable element 144, and LEDs 146. A communication device 140 (including an antenna if necessary) is also provided. Although the present inventions are not limited to any particular communication device, the exemplary communication device 140 is telemetry device that transmits an RF signal at a specified frequency. The RF signal may, in some instances, be a carrier signal that carriers bit streams. The communication device 140 is also configured to receive signals from the implantable infusion device 300. Other exemplary communication devices include oscillating magnetic field communication devices, static magnetic field communication devices, optical communication devices, ultrasound communication devices and direct electrical communication devices.

Figure 41:
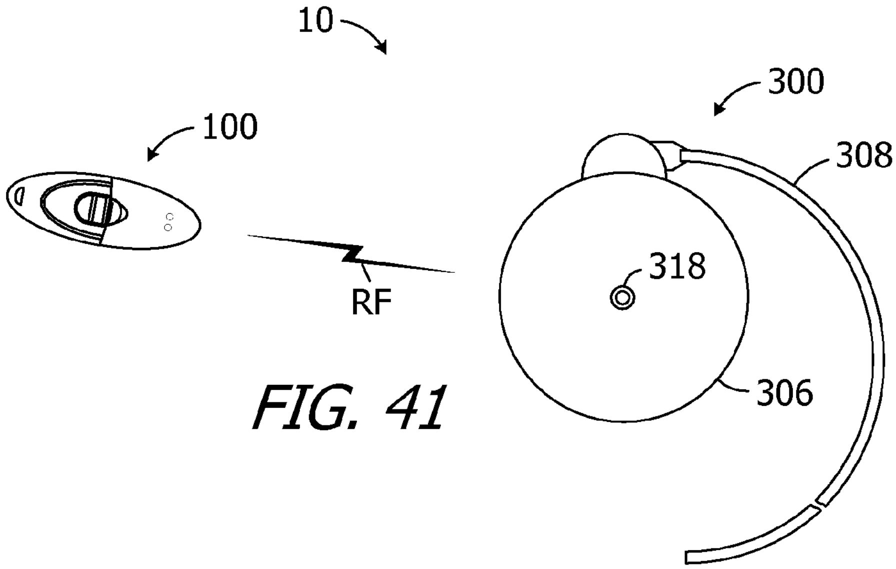
FIG. 41 is a plan view of an ambulatory medical device system in accordance with one embodiment of a present invention.
Figure 42:
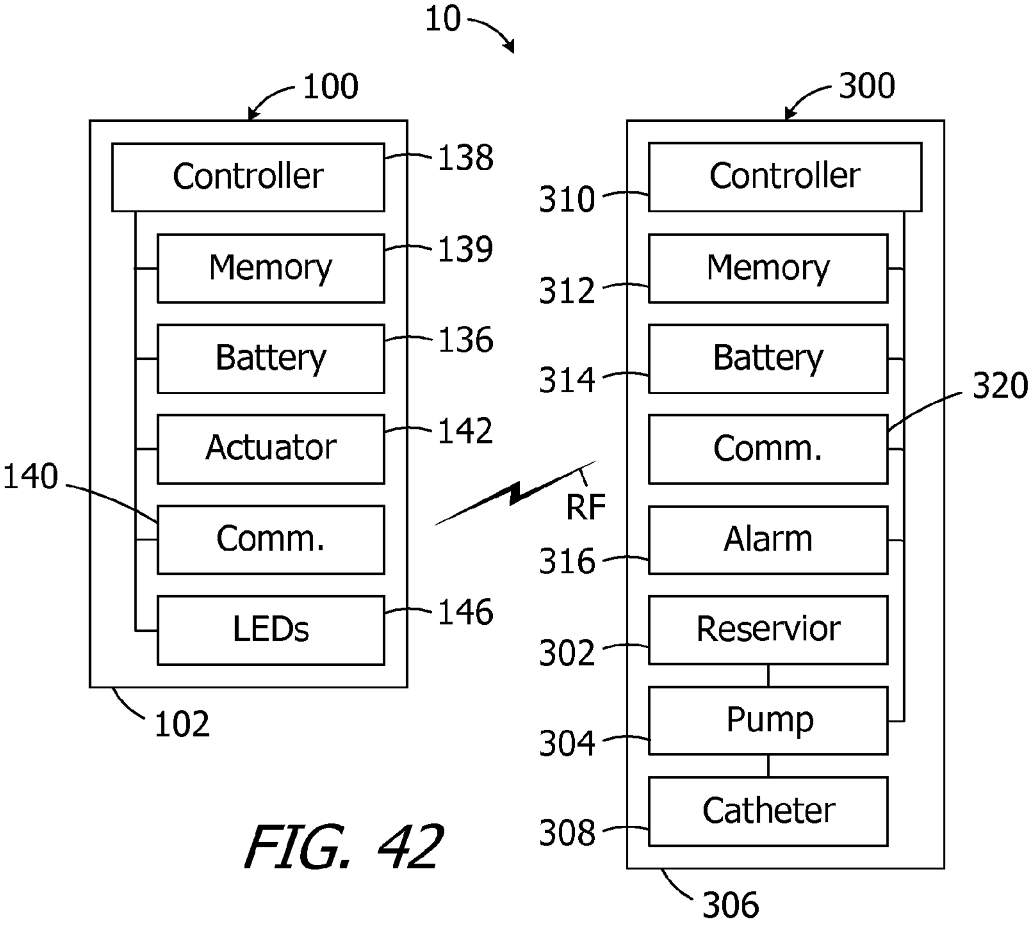
FIG. 42 is a block diagram of the ambulatory medical device system illustrated in FIG. 41.

The exemplary implantable infusion device 300 illustrated in FIGS. 41 and 42 includes a medication reservoir 302 and a pump or other fluid transfer device 304 within a housing 306. The pump 304 transfers medication from the reservoir 302 through a catheter 308 to the target region within the body. Operation of the implantable infusion device 300 is controlled by a controller 310, such as a microprocessor, microcontroller or other control circuitry, in accordance with instructions stored in memory 312. Power is provided by a battery or other power source 314. An audible alarm 316 may also be provided in order to inform the patient, for example, when the amount of medication in the reservoir 302 is low or when the amount of energy stored in the battery 314 is low. A refill port 318, which allows the reservoir to be refilled while the implantable infusion device 300 is within the patient, is positioned on the exterior of the housing 306.

A communication device 320 is also provided. The communication device 320 in the exemplary implantable infusion device 300 is configured to receive signals from, and transmit signals to, the remote control 100. To that end, the exemplary communication device 320 may be a telemetry device that transmits and receives RF signals at a specified frequency. The RF signal may, in some instances, be a carrier signal that carriers bit streams.

The remote control 100 may be used, for example, to send a "bolus delivery" request to the implantable infusion device 300 by way of the communication devices 140 and 320 when the button 104 is pressed. The remote control controller 138 may actuate one or more of the LEDs 146 in order to confirm to the patient that the "bolus delivery" request has been transmitted. The implantable infusion device controller 310 may respond to the receipt of the "bolus delivery" request in a variety of ways. For example, the controller 310 may accept the request, actuate the fluid transfer device 304, and transmit an "acceptance" signal to the remote control 100. In response to the "acceptance" signal, the remote control controller 138 may actuate one or more of the LEDs 146 so as to indicate that that the "bolus delivery" request has been accepted.

The controller 310 may, alternatively, deny the "bolus delivery" request because the fluid transfer device 304 is already in the process of transferring medication to the catheter 308, the patient has already reached the maximum permissible number of bolus deliveries for a particular time period, or there has not been sufficient time since the last delivery of medication. A "denial" signal may also be transmitted from the infusion device 300 to the remote control 100 and, in response, the remote control controller 138 may actuate one or more of the LEDs 146 so as to indicate that that the "bolus delivery" request has been denied.

Although the inventions disclosed herein have been described in terms of the preferred embodiments above, numerous modifications and/or additions to the above-described preferred embodiments would be readily apparent to one skilled in the art. By way of example, but not limitation, in an audible communication device (e.g. a buzzer) may be provided in place of, or in addition to, the LEDs 146 on the remote controls 100-100*h*. The inventions also include any combination of the elements from the various species and embodiments disclosed in the specification that are not already described. It is intended that the scope of the present inventions extend to all such modifications and/or additions and that the scope of the present inventions is limited solely by the claims set forth below. Additionally, the present inventions include systems that comprise an ambulatory medical device (such as an implantable infusion device) in combination with any of the remote controls described above or claimed below.

We claim:

1. A remote control for use with an implantable infusion device, the remote control comprising:
- only one button;
- means for implantable infusion device in response to pressing of the only one button; and
- means for preventing inadvertent medication delivery by preventing inadvertent pressing of the only one button.

2. A remote control as claimed in claim 1, wherein the only one button comprises an actuator and a cover.

3. A remote control for use with an implantable infusion device, the remote control comprising:
- a button;
- a button control element associated with the button and movable between a first position where the button is prevented from being pressed and a second position where the button is not prevented from being pressed; and
- means for wirelessly transmitting a medication delivery signal to the implantable infusion device in response to the button being pressed.

4. A remote control for use with an implantable infusion device as claimed in claim 3, wherein the button comprises an actuator and a cover.

5. A remote control for use with an implantable infusion device as claimed in claim 3, wherein the button control element is biased to the first position.

6. A remote control for use with an implantable infusion device as claimed in claim 3, further comprising:
- a housing that carries the button;
- wherein the button control element is secured to the housing and is movable relative to the housing.

7. A remote control for use with an implantable infusion device as claimed in claim 6, wherein
- the housing defines a longitudinal axis; and
- the button control element is longitudinally movable relative to the housing.

8. A remote control for use with an implantable infusion device as claimed in claim 3, wherein the button defines a first button and the button control element defines a first button control element, the remote control further comprising:
- a second button; and
- a second button control element associated with the second button and movable, independently of the first button control element, between a first position where the second button is substantially prevented from being pressed and a second position where the second button is not substantially prevented from being pressed.

9. A remote control for use with an implantable infusion device as claimed in claim 3, further comprising:
- a housing that carries the button;
- wherein the button control element pivots relative to the housing.

10. A remote control for use with an implantable infusion device as claimed in claim 9, wherein the button control element comprises a wire-like structure having a pivot end that is pivotably secured to the housing and a free end.

11. A remote control for use with an implantable infusion device as claimed in claim 10, further comprising:
- a sensor adapted to sense when the wire-like structure is in the second position.

12. A remote control for use with an implantable infusion device as claimed in claim 3, further comprising:

an elongate housing defining a first and second longitudinal ends and a longitudinal axis;

wherein the button and the button control element are associated with the first longitudinal end and the button control element is movable in a direction that is generally transverse to the longitudinal axis.

13. A remote control for use with an implantable infusion device as claimed in claim 3, further comprising:

a housing defining a longitudinal axis;

wherein the button moves longitudinally relative to the housing; and wherein the button control element comprises a detent and indentation arrangement associated with the button and the housing.

14. A remote control for use with an implantable infusion device as claimed in claim 3, wherein the button control element comprises a lock.

15. A remote control for use with an implantable infusion device as claimed in claim 3, wherein the button control element substantially covers the button when the button control element is in the first position.

16. A remote control for use with an implantable infusion device as claimed in claim 3, further comprising:

a housing that carries the button and is sized and shaped such that it may be carried by a human hand.

17. A remote control for use with an implantable infusion device as claimed in claim 3, wherein the button control element substantially prevents the button from being pressed when in the first position and the button control element does not substantially prevent the button from being pressed when in the second position.

18. A remote control for use with an implantable infusion device as claimed in claim 3, wherein the button control element prevents the button from being pressed by a human finger when in the first position and does not prevent the button from being pressed by a human finger when in the second position.

19. A remote control for use with an ambulatory medical device, the remote control comprising:

a button;

a housing that carries the button;

a button control element having a main portion that is secured to the housing and a depressible member that is pivotably secured to the main portion of the button control element and covers the button, the button control element being movable relative to housing between a first position where the button is substantially prevented from being pressed and a second position where the button is not substantially prevented from being pressed; and means for communicating with the ambulatory medical device in response to the button being pressed.

20. A remote control for use with an ambulatory medical device as claimed in claim 19, wherein the depressible member is biased away from the button.

21. A remote control for use with an ambulatory medical device, the remote control comprising:

a button;

a housing that carries the button;

means for communicating with the ambulatory medical device in response to the button being pressed; and a button control element including a main portion that is pivotably secured to the housing and a depressible member that is pivotably secured to the main portion of the button control element;

the button control element being movable between a first position where the button is substantially prevented from being pressed and a second position where the button is not substantially prevented from being pressed; and the button and button control element being respectively configured and positioned such that the main portion of the button control element covers the button when the button control element is in the first position and the depressible member covers the button when the button control element is in the second position.

22. A remote control for use with an ambulatory medical device, comprising:

a housing;

a communication device associated with the housing and adapted to communicate with the ambulatory medical device;

an actuator operably connected to the communication device; and a depressible member that is movable in a depression direction, that is operably connected to the housing, and that is also movable relative to the actuator and to the housing, in a direction that is at least transverse to the depression direction, between a first position where the depressible member is prevented from being depressed and a second position where the depressible member is substantially aligned with the actuator and is not prevented from being depressed.

23. A remote control for use with an ambulatory medical device as claimed in claim 22, wherein the actuator forms part of a button.

24. A remote control for use with an ambulatory medical device as claimed in claim 22, wherein the communication device comprises a radio frequency telemetry device.

25. A remote control for use with an ambulatory medical device as claimed in claim 22, wherein the depressible member is slidably carried relative to the housing.

26. A remote control for use with an ambulatory medical device as claimed in claim 22, wherein the housing defines a longitudinal axis; and the depressible member is longitudinally movable relative to the housing.

27. A remote control for use with an ambulatory medical device as claimed in claim 22, wherein the depressible member is pivotable in the depression direction.

28. A remote control for use with an ambulatory medical device as claimed in claim 22, wherein the depressible member is biased away from the actuator.

29. A remote control for use with an ambulatory medical device as claimed in claim 22, wherein the depressible member is biased to the first position.

30. A remote control for use with an ambulatory medical device as claimed in claim 22, wherein the actuator is depressible; and the configuration of the depressible member being such that it will contact the actuator when depressed.

31. A remote control for use with an ambulatory medical device as claimed in claim 22, wherein the depressible member is movable in a depression direction that is substantially perpendicular to the depression direction.

32. A remote control for use with an ambulatory medical device as claimed in claim 22, wherein the depressible member is part of a button control element.

* * * * *